(12) United States Patent
Leary et al.

(10) Patent No.: US 9,551,714 B2
(45) Date of Patent: Jan. 24, 2017

(54) MATERIALS AND METHODS FOR ASSAY OF ANTI-HEPATITIS C VIRUS (HCV) ANTIBODIES

(75) Inventors: Thomas P. Leary, Kenosha, WI (US); Robin A. Gutierrez, Gurnee, IL (US); A. Scott Muerhoff, Kenosha, WI (US); George J. Dawson, Libertyville, IL (US); Suresh M. Desai, Libertyville, IL (US); Dinesh Shah, Libertyville, IL (US)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 13/168,373

(22) Filed: Jun. 24, 2011

(65) Prior Publication Data

US 2012/0202295 A1    Aug. 9, 2012

Related U.S. Application Data

(60) Provisional application No. 61/358,494, filed on Jun. 25, 2010.

(51) Int. Cl.
*C07K 14/005* (2006.01)
*G01N 33/576* (2006.01)

(52) U.S. Cl.
CPC ......... *G01N 33/5767* (2013.01); *C07K 14/005* (2013.01); *C12N 2770/24222* (2013.01); *G01N 2333/186* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 4,470,461 A | 9/1984 | Stapp | |
| 4,554,101 A | 11/1985 | Hopp | |
| 4,870,008 A | 9/1989 | Brake | |
| 4,931,373 A | 6/1990 | Kawasaki et al. | |
| 5,006,309 A | 4/1991 | Khalil et al. | |
| 5,023,328 A | 6/1991 | Summers et al. | |
| 5,063,081 A | 11/1991 | Cozzette et al. | |
| 5,077,214 A | 12/1991 | Guarino et al. | |
| 5,089,424 A | 2/1992 | Khalil et al. | |
| 5,122,464 A | 6/1992 | Wilson et al. | |
| 5,135,875 A | 8/1992 | Meucci et al. | |
| 5,241,070 A | 8/1993 | Law | |
| 5,242,828 A | 9/1993 | Bergstrom et al. | |
| 5,294,404 A | 3/1994 | Grandone et al. | |
| 5,350,671 A | 9/1994 | Houghton et al. | |
| 5,352,803 A | 10/1994 | Mattingly | |
| 5,359,093 A | 10/1994 | Adamczyk et al. | |
| 5,411,749 A | 5/1995 | Mayo et al. | |
| 5,468,646 A | 11/1995 | Mattingly et al. | |
| 5,496,925 A | 3/1996 | Mattingly | |
| 5,543,524 A | 8/1996 | Mattingly et al. | |
| 5,573,904 A | 11/1996 | Mattingly | |
| 5,593,896 A | 1/1997 | Adamczyk et al. | |
| 5,679,543 A | 10/1997 | Lawlis | |
| 5,705,330 A * | 1/1998 | Shah et al. ................. 435/5 |
| 5,783,699 A | 7/1998 | Mattingly et al. | |
| 5,795,784 A | 8/1998 | Arnquist et al. | |
| 5,856,194 A | 1/1999 | Arnquist et al. | |
| 5,859,193 A | 1/1999 | Devare et al. | |
| 6,225,047 B1 | 5/2001 | Hutchens et al. | |
| 6,329,209 B1 | 12/2001 | Wagner et al. | |
| 6,727,092 B2 | 4/2004 | Stewart et al. | |
| 6,846,905 B2 | 1/2005 | Hackett, Jr. et al. | |
| 7,041,479 B2 | 5/2006 | Swartz et al. | |
| 7,906,293 B2 | 3/2011 | Mattingly et al. | |
| 2002/0090607 A1 | 7/2002 | Fields et al. | |
| 2003/0170881 A1 | 9/2003 | Davis et al. | |
| 2004/0018577 A1 | 1/2004 | Emerson Campbell et al. | |
| 2005/0054078 A1 | 3/2005 | Miller et al. | |
| 2006/0160164 A1 | 7/2006 | Miller et al. | |
| 2008/0020401 A1 | 1/2008 | Grenier et al. | |
| 2008/0248493 A1 | 10/2008 | Mattingly et al. | |

(Continued)

FOREIGN PATENT DOCUMENTS

| | | |
|---|---|---|
| EP | 0238023 A2 | 9/1987 |
| EP | 0338841 A1 | 10/1989 |

(Continued)

OTHER PUBLICATIONS

Nasoff MS, Zebedee SL, Inchauspé G, Prince AM. Identification of an immunodominant epitope within the capsid protein of hepatitis C virus. Proc Natl Acad Sci U S A. Jun. 15, 1991;88(12):5462-6.*
Nasoff MS, et al. Identification of an immunodominant epitope within the capsid protein of hepatitis C virus. Proc Natl Acad Sci U S A. Jun. 15, 1991;88(12):5462-6.*
Chang JC et al. Antigenic heterogeneity of the hepatitis C virus NS4 protein as modeled with synthetic peptides. Virology. Apr. 25, 1999;257(1):177-90.*
Chien DY et al. Diagnosis of hepatitis C virus (HCV) infection using an immunodominant chimeric polyprotein to capture circulating antibodies: reevaluation of the role of HCV in liver disease. Proc Natl Acad Sci U S A. Nov. 1, 1992;89(21):10011-5.*
Busch MP et al. A pattern of 5-1-1 and c100-3 only on hepatitis C virus (HCV) recombinant immunoblot assay does not reflect HCV infection in blood donors. Transfusion. Jan. 1993;33(1):84-8.*
PRF: 742039. Core protein [Hepatitis C virus]. Dated Nov. 15, 1992.*

(Continued)

*Primary Examiner* — Nick Zou
(74) *Attorney, Agent, or Firm* — Irene M. Reininger

(57) ABSTRACT

A polypeptide comprising the contiguous amino acids 1-198 of SEQ ID NO: 2; a polypeptide, which comprises a contiguous amino acid sequence that is at least about 95% identical to the contiguous amino acids 1-198 of SEQ ID NO: 2, an epitope that is immunoreactive with an antibody that specifically binds to the core protein of hepatitis C virus (HCV), and an epitope that is immunoreactive with an antibody that specifically binds to the NS4 region of HCV; a nucleic acid encoding such a polypeptide; a host cell comprising such a nucleic acid; an immunodiagnostic reagent comprising such a polypeptide; a kit comprising such an immunodiagnostic reagent; and a method of determining the presence, amount, or concentration of anti-HCV antibodies in a test sample.

7 Claims, 6 Drawing Sheets

(56) References Cited

U.S. PATENT DOCUMENTS

2010/0167301 A1 7/2010 Collier et al.

FOREIGN PATENT DOCUMENTS

| EP | 0471293 A2 | 2/1992 |
|---|---|---|
| EP | 0614984 A2 | 9/1994 |
| EP | 870830 A2 | 10/1998 |
| EP | 1004023 B1 | 11/2004 |
| EP | 2099825 A2 | 9/2009 |
| WO | WO8702670 A1 | 5/1987 |
| WO | WO9005783 A1 | 5/1990 |
| WO | WO9100906 A1 | 1/1991 |
| WO | WO9110741 A1 | 7/1991 |
| WO | WO9203918 A1 | 3/1992 |
| WO | WO9305796 A1 | 4/1993 |
| WO | WO9600787 A1 | 1/1996 |
| WO | WO9951773 A1 | 10/1999 |
| WO | WO0056934 A1 | 9/2000 |
| WO | WO2004039950 A2 | 5/2004 |
| WO | WO2008024518 A2 | 2/2008 |

OTHER PUBLICATIONS

GenBank: ADC54727.1. polyprotein, partial [Hepatitis C virus subtype 1 a]. Dated Feb. 17, 2010.*
GenBank: AAK66555.1. HCV type 1a polyprotein [synthetic construct]. Dated Jun. 24, 2001.*
Adamczyk M., et al., "Chemiluminescence Quenching of Pteroic Aacid-N-sulfonyl-acridinium-9-carboxamide Conjugates by Folate Binding Protein," Bioorganic & Medicinal Chemistry Letters, 2004, vol. 14 (9), pp. 2313-2317.
Adamczyk M., et al., "Chemiluminescent Acridinium-9-Carboxamide Boronic Acid Probes: Application to a Homogeneous Glycated Hemoglobin Assay," Bioorganic & Medicinal Chemistry Letters, 2006, vol. 16 (5), pp. 1324-1328.
Adamczyk M., et al., "Chemiluminescent N-Sulfonylacridinium-9-Carboxamides and Their Application in Clinical Assays," Luminescence Biotechnology: Instruments and Applications , 2002, pp. 77-105.
Adamczyk M., et al., "Homogeneous Chemiluminescent Assays for Free Choline in Human Plasma and Whole Blood," Analytica Chimica Acta, 2006, vol. 579 (1), pp. 61-67.
Adamczyk M., et al., "Intrinsic Factor-Mediated Modulation of Cyanocobalamin-N-sulfonyl-acridinium-9-carboxamide Chemiluminescence," Bioorganic & Medicinal Chemistry Letters, 2004, vol. 14 (15), pp. 3917-3921.
Adamczyk M., et al., "Linker-Medicated Modulation of the Cheiluminescent Signal from $N^{10}$-(3-Sulfopropyl)-N-Sulfonylacridinium-9-carboxamide Tracers," Bioconjugate Chemistry, 2000, vol. 11, pp. 714-724.
Adamczyk M., et al., "Modulation of the Chemiluminescent Signal from $N^{10}$-(3-Sulfopropyl)-N-Sulfonylacridinium-9-carboxamides," Tetrahedron, 1999, vol. 55, pp. 10899-10914.
Adamczyk M., et al., "Neopentyl 3-Triflyloxypropanesulfaonate Areactive Sulfopropylation Reagent for the Preparation of Chemiluminescent Labels," Journal of Organic Chemistry, 1998, vol. 63, pp. 5636-5639.
Adamczyk M., et al., "Regiodependent Luminescence Quenching of Biotinylated N-Sulfonyl-acridinium-9-carboxamides by Avidin ," Organic Letters, 2003, vol. 5 (21), pp. 3779-3782.
Adamczyk M., et al., "Synthesis of a Chemiluminescent Acridinium Hydroxylamine (AHA) for the Direct Detection of Abasic Sites in DNA," Organic Letters, 1999, vol. 1 (5), pp. 779-781.
Altschuel S.F., et al., "Basic Local Alignment Search Tool," Journal of Molecular Biology, 1990, 215 (3), 403-410.
Ausubel F.M., et al., "Current Protocols in Molecular Biology," 1996, vol. 1, pp. 1-14.
Becker D.M., et al., "High-Efficiency Transformation of Yeast by Electroporation," Methods in Enzymology, 1991, vol. 194, pp. 182-187.

Bernard H.U., et al., "Construction of Plasmid Cloning Vehicles that Promote Gene Expression from the Bacteriophage Lambda PI Promoter," Gene, 1979, vol. 5 (1), pp. 59-76.
Bird R.E., et al., "Single-Chain Antigen Binding Proteins," Science, 1988, vol. 242 (4877), pp. 423-426.
Bodanszky M., et al., "Active Esters and Resins in Peptide Synthesis," Chemistry and Industry, 1966, vol. 38, pp. 1597-1598.
Brennan M., et al., "Preparation of Bispecific Antibodies by Chemical Recombination of Monoclonal Immunoglobulin $G_1$ Fragments," Science, 1985, vol. 229, pp. 81-83.
Carter P., et al., "High Level *Escherichia coli* Expression and Production of a Bivalent Humanized Antibody Fragment," Biotechnology, 1992, vol. 10, pp. 163-167.
Cate R.L., et al., "Isolation of the Bovine and Human Genes for Müllerian Inhibiting Substance and Expression of the Human Gene in Animal Cells," Cell, 1986, vol. 45, pp. 685-696.
Chang S., et al., "High Frequency Transformation of *Bacillus subtilis* Protoplasts by Plasmid DNA," Molecular Genetics and Genomics, 1979, vol. 168, pp. 111-115.
Choo, et al., "Isolation of a cDNA Clone Derived from a Blood-Borne Non-A, Non-B Viral Hepatitis Genome", Science, 1989, vol. 244 (4902), pp. 359-362.
Cole S.P.C., et al., "The EBV-Hybridoma Technique and Its Application to Human Lung Cancer," Monoclonal Antibodies and Cancer Therapy, 1985, pp. 77-96.
Coloma J.M., et al., "Novel Vectors for the Expression of Antibody Molecules Using Variable Regions Generated by Polymerase Chain Reaction," Journal of Immunological Methods, 1992, vol. 152, pp. 89-104.
Co-pending U.S. Appl. No. 60/878,017, filed Dec. 29, 2006.
Co-pending U.S. Appl. No. 61/142,048, filed Dec. 31, 2008.
Dayhoff M.O., ed., Atlas of Protein Sequences and Structure, 5 (Suppl. 3), 1978, pp. 353-358.
Dubnaua D., et al., "Fate of Transforming DNA Following Uptake by Competent *Bacillus subtilis*," Journal of Molecular Biology, 1971, vol. 56, pp. 209-221.
Dupuis L., et al., "Influence of Various Signal Peptides on Secretion of Mammalian Acidic Lipases in Baculovirus-Insect Cell System," Methods in Enzymology, 1997, vol. 284, pp. 261-272.
Ganeva V., et al., "Influence of Glucose and Other Substrates on Electric Field and Polyethylene Glycol-mediated Transformation of Intact Yeast Cells," FEMS Microbiology Letters, 1994, vol. 121, pp. 159-164.
Gisin B.F., et al., "The Preparation of Merrifield-Resins Through Total Esterification with Cesium Salts," Helvetica Chimica Acta, 1973, vol. 56 (5), pp. 1476-1483.
Hagenbuchle O., et al., "Mouse Liver and Salivary Gland α-amylase mRNAs Differ Only in 5' Non-translated Sequences," Nature, 1981, vol. 289, pp. 643-646.
Harrison M.A., et al., "General Techniques of Cell Culture," A Practical Animal Cell Biology, 1997, pp. 1-3.
Haugland, et al., "Handbook of Fluorescent Probes and Research Chemicals," Molecular Probes, 1996, Table of Contents and pp. ix-xii.
Hinnen A., et al., "Transformation of Yeast," Proceedings of the National Academy of Sciences, 1978, vol. 75 (4), pp. 1929-1933.
Holliger P., et al., ""Diabodies": Small Bivalent and Bispecific Antibody Fragments," Proceedings of the National Academy of Sciences of the USA, 1993, vol. 90 (14), pp. 6444-6448.
Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences of the USA, 1988, vol. 85 (16), pp. 5879-5883.
Ito H., et al., "Transformation of Intact Yeast Cells Treated with Alkali Cations," Journal of Bacteriology, 1983, vol. 153 (1), pp. 163-168.
Jenkins N., et al., "Animal Cell Biotechnology Methods and Protocols," Methods in Bio technology, 1999, pp. 1-5.
Kaufman R.J., et al., "Construction of a Modular Dihydrofolate Reductase cDNA Gene: Analysis of Signals Utilized for Efficient Expression," Molecular and Cellular Biology, 1982, vol. 2 (11), pp. 1304-1319.

(56) References Cited

OTHER PUBLICATIONS

Kennett R.H., et al., eds., "Monoclonal Antibodies" in Hybridomas: A New Dimension in Biological Analyses, Plenum Press, 1980, Table of Contents.
Kim D.M.., et al., "Prolonging Cell-Free Protein Synthesis by Selective Reagent Additions," Biotechnology Progress, 2000, vol. 16 (3), pp. 385-390.
Kim D.M., et al., "Prolonging Cell-Free Protein Synthesis with a Novel ATP Regeneration System," Biotechnology and Bioengineering, 1999, vol. 66 (3), pp. 180-188.
Koehler T.M., et al., "*Bacillus subtilis* (*natto*) Plasmid pLS20 Mediates Interspecies Plasmid Transfer," Journal of Bacteriology, 1987, vol. 169 (11), pp. 5271-5278.
Kohler G., et al., "Continuous Cultures of Fused Cells Secreting Antibody of Predefined Specificity," Nature, 1975, vol. 256 (5517), pp. 495-497.
Kozak M., "At Least Six Nucleotides Preceding the AUG Initiator Codon Enhance Translation in Mammalian Cells," Journal of Molecular Biology, 1987, vol. 196, pp. 947-950.
Kozbor D., et al., "The Production of Monoclonal Antibodies from Human Lymphocytes," Immunology Today, 1983, vol. 4 (3), pp. 72-79.
Kyte J., et al., "A Simple Method for Displaying the Hydropathic Character of a Protein," Journal of Molecular Biology, 1982, vol. 157 (1), pp. 105-132.
Li A., et al., "Optimized Gene Synthesis and High Expression of Human Interleukin-18," Protein Expression and Purification, 2003, vol. 32 (1), pp. 110-118.
Malardier L., et al., "Cloning of the Nitrate Reductase Gene (niaD) of *Aspergillus nidulans* and its Use for Transformation of *Fusarium oxysporum*," Gene, 1989, vol. 78, pp. 147-156.
Manivasakam P., et al., "High Efficiency Transformation of *Saccharomyces Cerevisiae* by Electroporation," Nucleic Acids Research, 1993, vol. 21 (18), pp. 4414-4415.
Mattingly P.G., "Chemiluminescent 10-Methyl-Acridinium-9(N-Sulphonylcarboxamide) Salts. Synthesis and Kinetics of Light Emission," Journal of Bioluminescence and Chemiluminescence, 1991, vol. 6, pp. 107-114.
McCafferty J., et al., "Phage Antibodies: Filamentous Phage Displaying Antibody Variable Domains," Nature, 1990, vol. 348, pp. 552-554.
McCapra F., et al., "Chemiluminescence Involving Peroxide Decompositions," Photochemistry and Photobiology, 1965, vol. 4, pp. 1111-1121.
McCune J.M., et al., "The SCID-hu Mouse: Murine Model for the Analysis of Human Hematolymphiod Differentiation and Function," Science, 1988, vol. 241, pp. 1632-1639.
Merrifield R.B., et al., "Solid Phase Peptide Synthesis. I. The Synthesis of a Tetrapeptide," Journal of the American Chemical Society, 1963, vol. 85, pp. 2149-2154.
Mitani E.M., et al., "A Novel Aspartyl Protease Allowing *KEX2*-Independent MFα Propheromone Processing in Yeast," Yeast, 1990, vol. 6, pp. 127-137.
Morimoto K., et al., "Single-Step Purification of F(ab)$_2$ Fragments of Mouse Monoclonal Antibodies (Immunoglobulins G1) by Hydrophobic Interaction High Performance Liquid Chromatography Using TSKgel Phenyl-5PW," Journal of Biochemical and Biophysical Methods, 1992, vol. 24, pp. 107-117.
Murphy C., et al., "Enhanced Expression, Secretion, and Large-Scale Purification of Recombinant HIV-1 gp120 in Insect Cells Using the Baculovirus egt and p67 Signal Peptides," Protein Expression and Purification, 1993, vol. 4, pp. 349-357.
Noren C.J., et al., "A General Method for Site-Specific Incorporation of Unnatural Amino Acid into Protiens," Science, 1989, vol. 244 (4901), pp. 182-188.
Ogata, et al., "Nucleotide sequence and mutation rate of the H strain of hepatitis C virus", Proc. Natl. Acad. Sci. USA, 1991, 88, 3392-3396.
Okkels J., et al., "A URA3-Promoter Deletion in a pYES Vector Increases the Expression Level of a Fungal Lipase in *Saccharomyces Cerevisiae*," Annals New York Academy of Sciences, 1996, vol. 782, pp. 202-207.
Pace C.N., et al., "How to Measure and Predict the Molar Absorption Coefficient of a Protein," Protein Science, 1995, vol. 4 (11), pp. 2411-2423.
Pietta P.G., et al., "Amide Protection and Amide Supports in Solid-phase Peptide Synthesis," Chemical Communications, 1970, pp. 650-651.
Polak J.M., et al., Introduction to Immunocytochemistry, 2nd Edition, Springer-Verlag, 1997, Table of Contents.
Poljak R.J., "Production and Structure of Diabodies," Structure, 1994, vol. 2 (12), pp. 1121-1123.
Quinn Frank A., "36 Bulk Reagent Random-Access Analyzer: ARCHITECT® i2000®," The Immunoassay Handbook, 2001, 2, Wild D., Ed., 363-367.
Razavi Z., et al., "Stable and Versatile Active Acridinium Esters I ," Luminescence, 2000, vol. 15 (4), pp. 239-244.
Razavi Z., et al., "Stable and Versatile Active Acridinium Esters II ," Luminescence, 2000, vol. 15, pp. 245-249.
Reeves E., et al., "Multiple Transformation of *Saccharomyces Cerevisiae* by Protoplast Fusion," FEMS Microbiology Letters, 1992, vol. 99, pp. 193-198.
Russell P.R., et al., "Transcription of the Triose-Phosphate-Isomerase Gene of *Schizosaccharomyces Pombe* Initiates from a Start Point Different from that in *Saccharomyces Cerevisiae*," Gene, 1985, vol. 40, pp. 125-130.
Sambrook J., et al., "Molecular Cloning: A Laboratory Manual," 1989, 2nd Ed., Cold Spring Harbor Laboratory Press, Table of Contents.
Shigekawa K., et al., "Electroporation of Eukaryotes and Prokaryotes: A General Approach to the Introduction of Macromolecules into Cells," Bio techniques, 1988, vol. 6 (8), pp. 742-751.
Simmonds P., et al., "Classification of hepatitis C virus into six major genotypes and a series of subtypes by phylogenetic analysis of the NS-5 region", The Journal of General Virology, 1993, 74 (11), Reading, UK, 2391-2399.
Smith T.F., "Comparison of Biosequences," Advances in Applied Mathematics, 1981, 2, 482-489.
Smith T.F., et al., "Identification of Common Molecular Subsequences," The Journal of Molecular Biology, 1981, vol. 147 (1), pp. 195-197.
Stewart J.M., et al., Solid Phase Peptide Synthesis, 2nd Edition, Pierce Chemical Company, 1984, Table of Contents.
Valls L.A., et al., "Protein Sorting in Yeast: The Localization Determinant of Yeast Vacuolar Carboxypeptidase Y Resides in the Propeptide," Cell, 1987, vol. 48, pp. 887-897.
Wallemacq P.E., et al., "Evaluation of the New AxSYM Cyclosporine Assay: Comparison with TDx Monoclonal Whole Blood and Emit Cyclosporine Assays," Clinical Chemistry, 1999, vol. 45 (3), pp. 432-435.
Wands J.R., et al., "High Affinity Monoclonal Antibodies to Hepatitis B Surface Antigen (HB$_s$Ag) Produced by Somatic Cell Hybrids," Gastroenterology, 1981, vol. 80 (2), pp. 225-232.
Wells D.A., et al., "High Throughput Bioanalytical Sample Preparation: Methods and Automation Strategies," Progress in Pharmaceutical and Biomedical Analysis, 2003, Table of Contents.
Yatscoff R.W., et al., "Abbott TDx Monoclonal Antibody Assay Evaluated for Measuring Cyclosporine in Whole Blood," Clinical Chemistry, 1990, vol. 36 (11), pp. 1969-1973.
Young F.E., et al., "Physiological and Genetic Factors Affecting Transformation of *Bacillus Subtilis*," Journal of Bacteriology, 1961, vol. 81, pp. 823-829.
Beld M., et al., "Quantitative Antibody Responses to Structural (Core) and Nonstructural (NS3, NS4, and NS5) Hepatitis C Virus Proteins among Seroconverting Injecting Drug Users: Impact of Epitope Variation and Relationship to Detection of HCV RNA in Blood," Hepatology, 1999, vol. 29 (4), pp. 1288-1298.
Chien D.Y., et al., "Use of a Novel Hepatitis C Virus (HCV) Major-Epitope Chimeric Polypeptide for Diagnosis of HCV Infection," Journal of Clinical Microbiology, 1999, vol. 37 (5), pp. 1393-1397.

(56) References Cited

OTHER PUBLICATIONS

International Search Report and Written Opinion for Application No. PCT/US2011/041760, mailed on Sep. 21, 2011, 15 pages.

Lin S., et al., "Design of Novel Conformational and Genotype-Specific Antigens for Improving Sensitivity of Immunoassays for Hepatitis C Virus-Specific Antibodies," Journal of Clinical Microbiology, 2005, vol. 43 (8), pp. 3917-3924.

Park Y.M., et al., "Monitoring Antibody Titers to Recombinant Core-NS3 Fusion Polypeptide is Useful for Evaluating Hepatitis C Virus Infection and Responses to Interferon-Alpha Therapy," Journal of Korean Medical Science, 1999, vol. 14 (2), pp. 165-170.

Sillanpaa M., et al., "Hepatitis C Virus Core, NS3, NS4B and NS5A are the Major Immunogenic Proteins in Humoral Immunity in Chronic HCV Infection," Virology Journal, 2009, vol. 6:84, 12 pages.

Zeng R., et al., "A Novel Combined Vaccine Candidate containing Epitopes of HCV NS3, Core and E1 Proteins induces Multi-Specific Immune Responses in BALB/c Mice," Antiviral Research, 2009, vol. 84 (1), pp. 23-30.

* cited by examiner

```
  1 GAATTCCATGCAGAAAAAAAAACAAACGTAACACCAACCGTCGTCCGCAGGACGTTAAATT
      MetGlnLysLysAsnLysArgAsnThrAsnArgArgProGlnAspValLysPhe·

61 CCCGGGTGGTGGTCAGATCGTTGGTGGTGTTTACCTGCTGCCGCGTCGTGGTCCGCGTCT
     ·ProGlyGlyGlyGlnIleValGlyGlyValTyrLeuLeuProArgArgGlyProArgLeu·

121 GGGTGTTCGTGCTACGCGTAAAACCTCTGAACGTTCTCAGCCGCGTGGGCGTCGTCAGCC
     ·GlyValArgAlaThrArgLysThrSerGluArgSerGlnProArgGlyArgArgGlnPro·

181 GATCCCGAAAGCTCGTCGTCCGGAAGGTCGTACCTGGGCTCAGCCGGGTTACCCGTGGCC
     ·IleProLysAlaArgArgProGluGlyArgThrTrpAlaGlnProGlyTyrProTrpPro·

241 GCTGTACGGTAACGAAGGTTGCGGTTGGGCTGGTTGGCTGCTGTCTCCGCGTGGATCTCG
     ·LeuTyrGlyAsnGluGlyCysGlyTrpAlaGlyTrpLeuLeuSerProArgGlySerArg·

301 TCCGTCTTGGGGTCCGACCGACCCGCGTCGTCGTTCTCGTAACCTTGGTAAAGTTATCGA
     ·ProSerTrpGlyProThrAspProArgArgArgSerArgAsnLeuGlyLysValIleAsp·

361 TACCCTGTCTGGTAAACCGGCCATTATCCCGGACCGTGAAGTTCTGTACCGTGAGTTCGA
     ·ThrLeuSerGlyLysProAlaIleIleProAspArgGluValLeuTyrArgGluPheAsp·

421 CGAAATGGAAGAATGCTCTCAGCACCTGCCGTACATCGAACAGGGTATGATGCTGGCTGA
     ·GluMetGluGluCysSerGlnHisLeuProTyrIleGluGlnGlyMetMetLeuAlaGlu·

481 ACAGTTCAAACAGAAAGCTCTGGGTCTGCTGCAGACCGCTTCTTGGATGAACCGTCTGAT
     ·GlnPheLysGlnLysAlaLeuGlyLeuLeuGlnThrAlaSerTrpMetAsnArgLeuIle·

541 CGCTTTCGCTTCTCGTGGTAACCACGTTTCTCCAACCCACTACGTTCCGGAATCGGACGC
     ·AlaPheAlaSerArgGlyAsnHisValSerProThrHisTyrValProGluSerAspAla·

601 TCATCATCACCATCACCATTGAGGATCC   [SEQ ID NO: 1]
     ·HisHisHisHisHisHis   [SEQ ID NO: 2]
```

FIG.1

```
MetGlnLysLysAsnLysArgAsnThrAsnArgArgProGlnAspValLysPhe    18
ProGlyGlyGlyGlnIleValGlyGlyValTyrLeuLeuProArgArgGlyPro    36
ArgLeuGlyValArgAlaThrArgLysThrSerGluArgSerGlnProArgGly   54
ArgArgGlnProIleProLysAlaArgArgProGluGlyArgThrTrpAlaGln   72
ProGlyTyrProTrpProLeuTyrGlyAsnGluGlyCysGlyTrpAlaGlyTrp   90
LeuLeuSerProArgGlySerArgProSerTrpGlyProThrAspProArgArg   108
ArgSerArgAsnLeuGlyLysValIleAspThrLeuSerGlyLysProAlaIle   126
IleProAspArgGluValLeuTyrArgGluPheAspGluMetGluGluCysSer   144
GlnHisLeuProTyrIleGluGlnGlyMetMetLeuAlaGluGlnPheLysGln   162
LysAlaLeuGlyLeuLeuGlnThrAlaSerTrpMetAsnArgLeuIleAlaPhe   180
AlaSerArgGlyAsnHisValSerProThrHisTyrValProGluSerAspAla   198
HisHisHisHisHisHis [SEQ ID NO: 2]                         204
```

FIG.2

```
  1 GAATTCCATGGCTGTTGACTTTATCCCGGTTGAAAATCTCGAGACTACTATGCGTTCTCC
        MetAlaValAspPheIleProValGluAsnLeuGluThrThrMetArgSerPro·

61 GGTTTTCACTGACAACTCTTCTCCGCCGGTTGTTCCGCAGTCTTTCCAGGTTGCTCACCT
    ·ValPheThrAspAsnSerSerProProValValProGlnSerPheGlnValAlaHisLeu·

121 GCATGCTCCGACTGGTTCTGGTAAATCTACTAAAGTTCCAGCTGCTTACGCTGCTCAGGG
    ·HisAlaProThrGlySerGlyLysSerThrLysValProAlaAlaTyrAlaAlaGlnGly·

181 TTACAAAGTTCTGGTTCTGAACCCGTCTGTTGCTGCTACTCTGGGTTTCGGCGCCTACAT
    ·TyrLysValLeuValLeuAsnProSerValAlaAlaThrLeuGlyPheGlyAlaTyrMet·

241 GTCTAAAGCTCACGGTATCGACCCGAACATTCGTACTGGTGTACGTACTATCACTACTGG
    ·SerLysAlaHisGlyIleAspProAsnIleArgThrGlyValArgThrIleThrThrGly·

301 TTCTCCGATCACTTACTCTACTTACGGTAAATTCCTGGCTGACGGTGGTTGCTCTGGTGG
    ·SerProIleThrTyrSerThrTyrGlyLysPheLeuAlaAspGlyGlyCysSerGlyGly·

361 TGCTTACGATATCATCATCTGCGACGAATGCCACTCTACTGACGCTACTTCTATCCTGGG
    ·AlaTyrAspIleIleIleCysAspGluCysHisSerThrAspAlaThrSerIleLeuGly·

421 TATCGGTACCGTTCTGGACCAGGCTGAAACTGCAGGTGCTCGTCTGGTTGTTCTGGCTAC
    ·IleGlyThrValLeuAspGlnAlaGluThrAlaGlyAlaArgLeuValValLeuAlaThr·

481 TGCTACTCCGCCGGGTTCTGTTACTGTTCCGCACCCGAACATCGAAGAAGTTGCTCTGTC
    ·AlaThrProProGlySerValThrValProHisProAsnIleGluGluValAlaLeuSer·

541 GACTACTGGTGAAATCCCGTTCTACGGTAAAGCTATCCCGCTCGAGGTTATCAAAGGTGG
    ·ThrThrGlyGluIleProPheTyrGlyLysAlaIleProLeuGluValIleLysGlyGly·

601 TCGTCACCTGATTTTCTGCCACTCTAAAAAAAAATGCGACGAACTGGCTGCTAAGCTTGT
    ·ArgHisLeuIlePheCysHisSerLysLysLysCysAspGluLeuAlaAlaLysLeuVal·
```

FIG.3A

661  TGCTCTGGGTATCAACGCTGTTGCTTACTACCGTGGTCTGGACGTTTCTGTTATCCCGAC
     ·AlaLeuGlyIleAsnAlaValAlaTyrTyrArgGlyLeuAspValSerValIleProThr·

721  TTCTGGTGACGTTGTTGTTGTGGCCACTGACGCTCTGATGACTGGTTACACTGGTGACTT
     ·SerGlyAspValValValValAlaThrAspAlaLeuMetThrGlyTyrThrGlyAspPhe·

781  CGACTCTGTTATCGATTGCAACACTTGC<u>AATTCC</u>ATGTCTACCAACCCGAAACCGCAGAA
     ·AspSerValIleAspCysAsnThrCys<u>AsnSer</u>MetSerThrAsnProLysProGlnLys·

841  AAAAAACAAACGTAACACCAACCGTCGTCCGCAGGACGTTAAATTCCCGGGTGGTGGTCA
     ·LysAsnLysArgAsnThrAsnArgArgProGlnAspValLysPheProGlyGlyGlyGln·

901  GATCGTTGGTGGTGTTTACCTGCTGCCGCGTCGTGGTCCGCGTCTGGGTGTTCGTGCTAC
     ·IleValGlyGlyValTyrLeuLeuProArgArgGlyProArgLeuGlyValArgAlaThr·

961  GCGTAAAACCTCTGAACGTTCTCAGCCGCGTGGGCGTCGTCAGCCGATCCCGAAAGCTCG
     ·ArgLysThrSerGluArgSerGlnProArgGlyArgArgGlnProIleProLysAlaArg·

1021 TCGTCCGGAAGGTCGTACCTGGGCTCAGCCGGGTTACCCGTGGCCGCTGTACGGTAACGA
     ·ArgProGluGlyArgThrTrpAlaGlnProGlyTyrProTrpProLeuTyrGlyAsnGlu·

1081 AGGTTGCGGTTGGGCTGGTTGGCTGCTGTCTCCGCGTGGATCTCGTCCGTCTTGGGGTCC
     ·GlyCysGlyTrpAlaGlyTrpLeuLeuSerProArgGlySerArgProSerTrpGlyPro·

1141 GACCGACCCGCGTCGTCGTTCTCGTAACCTTGGTAAAGTTATCGATACCCTGACCTGCGG
     ·ThrAspProArgArgArgSerArgAsnLeuGlyLysValIleAspThrLeuThrCysGly·

1201 TTTCGCTGACCTGATGGGTTACATACCGCTGGTTGGAGCTCCGCTGGGTGGTGCTGCTCG
     ·PheAlaAspLeuMetGlyTyrIleProLeuValGlyAlaProLeuGlyGlyAlaAlaArg·

1261 TGCTGGTTCTGGCAGCCATCATCACCATCACCATTGAGGATCC [SEQ ID NO: 3]
     ·AlaGlySerGlySerHisHisHisHisHisHis  [SEQ ID NO: 4]

FIG.3B

```
MetAlaValAspPheIleProValGluAsnLeuGluThrThrMetArgSerPro  18
ValPheThrAspAsnSerSerProProValValProGlnSerPheGlnValAla  36
HisLeuHisAlaProThrGlySerGlyLysSerThrLysValProAlaAlaTyr  54
AlaAlaGlnGlyTyrLysValLeuValLeuAsnProSerValAlaAlaThrLeu  72
GlyPheGlyAlaTyrMetSerLysAlaHisGlyIleAspProAsnIleArgThr  90
GlyValArgThrIleThrThrGlySerProIleThrTyrSerThrTyrGlyLys 108
PheLeuAlaAspGlyGlyCysSerGlyGlyAlaTyrAspIleIleIleCysAsp 126
GluCysHisSerThrAspAlaThrSerIleLeuGlyIleGlyThrValLeuAsp 144
GlnAlaGluThrAlaGlyAlaArgLeuValValLeuAlaThrAlaThrProPro 162
GlySerValThrValProHisProAsnIleGluGluValAlaLeuSerThrThr 180
GlyGluIleProPheTyrGlyLysAlaIleProLeuGluValIleLysGlyGly 198
ArgHisLeuIlePheCysHisSerLysLysLysCysAspGluLeuAlaAlaLys 216
LeuValAlaLeuGlyIleAsnAlaValAlaTyrTyrArgGlyLeuAspValSer 234
ValIleProThrSerGlyAspValValValValAlaThrAspAlaLeuMetThr 252
GlyTyrThrGlyAspPheAspSerValIleAspCysAsnThrCysAsnSerMet 270
SerThrAsnProLysProGlnLysLysAsnLysArgAsnThrAsnArgArgPro 288
GlnAspValLysPheProGlyGlyGlyGlnIleValGlyGlyValTyrLeuLeu 306
ProArgArgGlyProArgLeuGlyValArgAlaThrArgLysThrSerGluArg 324
SerGlnProArgGlyArgArgGlnProIleProLysAlaArgArgProGluGly 342
ArgThrTrpAlaGlnProGlyTyrProTrpProLeuTyrGlyAsnGluGlyCys 360
GlyTrpAlaGlyTrpLeuLeuSerProArgGlySerArgProSerTrpGlyPro 378
ThrAspProArgArgArgSerArgAsnLeuGlyLysValIleAspThrLeuThr 396
CysGlyPheAlaAspLeuMetGlyTyrIleProLeuValGlyAlaProLeuGly 414
GlyAlaAlaArgAlaGlySerGlySerHisHisHisHisHisHis           429
[SEQ ID NO: 4]
```

FIG.4

MATERIALS AND METHODS FOR ASSAY OF ANTI-HEPATITIS C VIRUS (HCV) ANTIBODIES

This application is a Non-provisional of U.S. Patent Application Ser. No. 61/358,494 filed on Jun. 25, 2010, which is incorporated herein by reference.

SEQUENCE LISTING

The instant application contains a Sequence Listing which has been submitted in ASCII format via EFS-Web and is hereby incorporated by reference in its entirety. Said ASCII copy, created on Jun. 24, 2011, is named 1549USO1.txt and is 16,154 bytes in size.

TECHNICAL FIELD

The present disclosure relates to polypeptides, including fusions thereof, nucleic acids, vectors, host cells, immunodiagnostic reagents, kits, and immunoassays.

BACKGROUND

Patient care as well as the prevention and transmission of Hepatitis C Virus (HCV) by blood and blood products or by close personal contact require sensitive, specific methods for screening and identifying carriers of HCV and HCV-contaminated blood or blood products. Serological determination of HCV exposure relies upon the detection of anti-HCV antibodies present in human blood plasma or sera. These anti-HCV antibodies are directed against a number of distinct structural and non-structural proteins encoded by the virus.

The genomic sequence of HCV is known, as are methods for obtaining the sequence. HCV has a 9.5 kb positive-sense, single-stranded RNA genome and is a member of the Flaviviridae family of viruses. Based on phylogenetic analysis, at least six distinct, but related, genotypes of HCV have been identified (Simmonds et al., J. Gen. Virol. 74: 2391-2399 (1993)).

The virus encodes a single polyprotein having more than 3,000 amino acid residues (Choo et al., Science 244: 359-362 (1989)). The polyprotein is processed co- and post-translationally into both structural and non-structural proteins. The polyprotein is cleaved into the following products: NH$_2$-C-E1-E2-P7-NS2-NS3-NS4a-NS4b-NS5a-NS5b-COOH. Initial cleavage of the polyprotein is catalyzed by host proteases, which liberate three structural proteins, the N-terminal nucleocapsid protein (called "core" and designated "C") and two envelope glycoproteins "E1" (also known as E) and "E2" (also known as E2/NS1), as well as nonstructural (NS) proteins that contain the viral enzymes. The NS regions are termed NS2, NS3, NS4, NS4a, NS4b, NS5a and NS5b.

Most commercial serological assays utilize an indirect format in which anti-HCV antibodies are captured by recombinant HCV antigens present on a solid phase, followed by detection of the anti-HCV antibody by a labeled anti-human antibody conjugate. While some of the antigenic regions of HCV have been identified, peptides and recombinant proteins from these regions exhibit a variable degree of sensitivity and selectivity in detection and diagnosis of HCV carriers. HC43 is one such recombinant protein used for the detection of HCV antibodies in human serum or plasma (SEQ ID NO: 4). HC43 contains the 33c region of the NS3 protein (HCV-1 amino acids 1192-1457) and the core or nucleocapsid structural protein (HCV-1 amino acids 1-150). HC43 is expressed in *E. coli* as a non-fusion protein by using a plasmid (pKRR826) containing the pL promoter of bacteriophage lambda (described in U.S. Pat. No. 6,846,905), utilizing a codon-optimized sequence from the HCV H strain (i.e., HCV-1; Ogata et al., PNAS USA 88: 3392-3396 (1991)). Two non-HCV coding amino acids separate the NS3 and core sequences. Another such recombinant protein used for the detection of anti-HCV antibodies is C100. This recombinant protein is derived from the NS4 region of the HCV genome (HCV amino acids 1569-1931), and is expressed in yeast with an N-terminal superoxide dismutase (SOD) fusion of 527 amino acids (see, e.g., U.S. Pat. No. 5,350,671). Although 363 amino acids of the HCV genome are present in the recombinant protein, studies have demonstrated that the majority of antibody binding occurs in two smaller regions within the NS4 region. The first region is the 5-1-1 region, which comprises HCV amino acids 1691-1733, and the second is the C100 region compromising HCV amino acids 1921-1940.

Previous attempts to express large regions of the HCV nonstructural regions (i.e., amino acids 1569-1931), including NS4a and NS4b, resulted in poor expression in *E. coli*. Thus, there is a need for HCV antigens, which comprise core and NS4 epitopes immunoreactive with anti-HCV antibodies and which can be expressed at high levels in bacteria, such as *E. coli*.

In view of the foregoing, the present disclosure seeks to provide such HCV antigens. This and other objects and advantages, as well as additional inventive features, will become apparent from the detailed description provided herein.

SUMMARY

An isolated or purified polypeptide comprising the contiguous amino acids 1-198 of SEQ ID NO: 2 is provided.

Also provided is an isolated or purified polypeptide comprising a contiguous amino acid sequence that is at least about 95% identical to the contiguous amino acids 1-198 of SEQ ID NO: 2. The polypeptide comprises (i) an epitope that is immunoreactive with an antibody that specifically binds to the core protein of hepatitis C virus (HCV) and (ii) an epitope that is immunoreactive with an antibody that specifically binds to the NS4 region of HCV.

In view of the above, also provided is an isolated or purified nucleic acid encoding a polypeptide comprising the contiguous amino acids 1-198 of SEQ ID NO: 2. The isolated or purified nucleic acid is optionally contained within a vector. The isolated or purified nucleic acid can comprise nucleotides 1-594 of SEQ ID NO: 1.

Also in view of the above, an isolated or purified nucleic acid encoding a polypeptide comprising a contiguous amino acid sequence that is at least about 95% identical to the contiguous amino acids 1-198 of SEQ ID NO: 2 is provided. The polypeptide comprises (i) an epitope that is immunoreactive with an antibody that specifically binds to the core protein of HCV and (ii) an epitope that is immunoreactive with an antibody that specifically binds to the NS4 region of HCV. The isolated or purified nucleic acid is optionally contained within a vector.

A host cell comprising an above-described isolated or purified nucleic acid is also provided. A preferred host cell is *Escherichia coli* (*E. coli*). When *E. coli* is the host cell, the isolated or purified nucleic acid is preferably operably linked with the $P_{Lambda}$ (pL) promoter.

Further provided is an immunodiagnostic reagent comprising (i) an above-described isolated or purified polypeptide and (ii) an isolated or purified polypeptide comprising an epitope that is immunoreactive with an antibody that specifically binds to the NS3 region of HCV. The isolated or purified polypeptide comprising an epitope that is immunoreactive with an antibody that specifically binds to the NS3 region of HCV can comprise the contiguous amino acids 1192-1457 of HCV. The isolated or purified polypeptide, which comprises an epitope that is immunoreactive with an antibody that specifically binds to the NS3 region of HCV, can further comprise an epitope that is immunoreactive with an antibody that specifically binds to the core region of HCV. The isolated or purified polypeptide, which comprises (i) an epitope that is immunoreactive with an antibody that specifically binds to the NS3 region of HCV and (ii) an epitope that is immunoreactive with an antibody that specifically binds to the core region of HCV, can comprise the contiguous amino acids 1192-1457 and 1-150 of HCV. The polypeptides of which the immunodiagnostic reagent is comprised can be coated on microparticles. In this regard, the polypeptides of which the immunodiagnostic reagent is comprised can be co-coated on the same microparticles. When the polypeptides are co-coated on the same microparticles, preferably the polypeptides (i) and (ii) are co-coated in a ratio of about 1:2 to about 1:6, wherein, when (i) and (ii) are co-coated on the same microparticles in a ratio of about 1:2, the concentration of (i) is at least about 40 µg/mL and the concentration of (ii) is at least about 80 µg/mL.

Still further provided is a kit comprising an above-described immunodiagnostic reagent and instructions for the use of the immunodiagnostic reagent in the immunoassay of anti-HCV antibodies.

Even still further provided is a method of determining the presence, amount, or concentration of anti-HCV antibodies in a test sample. The method comprises assaying the test sample for anti-HCV antibodies by an assay (i) employing (i') an above-described immunodiagnostic reagent, which comprises at least one pair of first specific binding partners, and (ii') at least one detectable label, and (ii) comprising comparing a signal generated by the detectable label as a direct or indirect indication of the presence, amount or concentration of anti-HCV antibodies in the test sample to a signal generated as a direct or indirect indication of the presence, amount or concentration of anti-HCV antibodies in a control or calibrator. The calibrator is optionally part of a series of calibrators in which each of the calibrators differs from the other calibrators in the series by the concentration of anti-HCV antibodies. The method can comprise (i) contacting the test sample with the immunodiagnostic reagent so as to form first specific binding partner/anti-HCV antibody complexes, (ii) contacting the first specific binding partner/anti-HCV antibody complexes with at least one detectably labeled second specific binding partner for anti-HCV antibody so as to form first specific binding partner/anti-HCV antibody/second specific binding partner complexes, and (iii) determining the presence, amount or concentration of anti-HCV antibodies in the test sample by detecting or measuring the signal generated by the detectable label in the first specific binding partner/anti-HCV antibody/second specific binding partner complexes formed in (ii). Alternatively, the method can comprise (i) contacting the test sample with the immunodiagnostic reagent and simultaneously or sequentially, in either order, contacting the test sample with at least one detectably labeled second specific binding partner, which can compete with anti-HCV antibody for binding to the at least one pair of first specific binding partners and which comprises detectably labeled anti-HCV antibodies, wherein any anti-HCV antibody present in the test sample and the at least one detectably labeled second specific binding partner compete with each other to form first specific binding partner/anti-HCV antibody complexes and a first specific binding partner/second specific binding partner complexes, respectively, and (ii) determining the presence, amount or concentration of anti-HCV antibodies in the test sample by detecting or measuring the signal generated by the detectable label in the first specific binding partner/second specific binding partner complex formed in (ii), wherein the signal generated by the detectable label in the first specific binding partner/second specific binding partner complex is inversely proportional to the amount or concentration of anti-HCV antibodies in the test sample. The polypeptides of which the immunodiagnostic reagent is comprised can be coated on microparticles. In this regard, the polypeptides of which the immunodiagnostic reagent is comprised can be co-coated on the same microparticles. When the polypeptides are co-coated on the same microparticles, preferably the polypeptides (i) and (ii) of the immunodiagnostic reagent are co-coated in a ratio of about 1:2 to about 1:6, wherein, when (i) and (ii) are co-coated on the same microparticles in a ratio of about 1:2, the concentration of (i) is at least about 40 µg/mL and the concentration of (ii) is at least about 80 µg/mL. When the test sample is obtained from a patient, the method can further comprise diagnosing, prognosticating, or assessing the efficacy of a therapeutic/prophylactic treatment of the patient. If the method further comprises assessing the efficacy of a therapeutic/prophylactic treatment of the patient, the method can optionally further comprise modifying the therapeutic/prophylactic treatment of the patient as needed to improve efficacy. The method can be adapted for use in an automated system or a semi-automated system.

BRIEF DESCRIPTION OF THE FIGURES

FIG. 1 is the nucleotide sequence encoding the HCV-1 core (amino acids 8-125) and NS4 fusion protein (amino acids 1688-1740 and 1915-1940) and a carboxyl-terminal hexa-histidine (6×His) tag (SEQ ID NO: 5) followed by the stop codon TGA (SEQ ID NO: 1). The translated amino acid sequence (SEQ ID NO: 2) is shown below the nucleotide sequence. The expression plasmid and expressed protein are referred to herein as p9NB44H and 9NB44H, respectively. The translated amino acid sequence is flanked by restriction endonuclease recognition sites (Eco RI at the 5' end and Bam HI at the 3' end), which are not translated.

FIG. 2 is the amino acid sequence of the 9NB44H HCV core-NS4 fusion protein (SEQ ID NO: 2).

FIG. 3 is the nucleotide sequence encoding the HCV-1 NS3 (amino acids 1192-1457) and core (amino acids 1-150) regions followed by a four codon linker sequence (encoding Gly Ser Gly Ser (SEQ ID NO: 6)) and a carboxyl-terminal 6×His tag (SEQ ID NO: 5) followed by a stop codon (SEQ ID NO: 3). The translated amino acid sequence is shown below the nucleotide sequence (SEQ ID NO: 4). The expression plasmid and expressed protein are referred to as pHC43H and HC43H, respectively. The translated sequence is flanked by restriction endonuclease recognition sites (Eco RI at the 5' end and Bam HI at the 3' end), which are not translated. The HCV NS3 and core encoded regions are separated by two codons (AAT TCC; underlined in nucleotide sequence), which are not derived from HCV-1 amino acids but which were introduced to facilitate cloning and expression.

FIG. 4 is the amino acid sequence of HC43H NS3-core fusion protein (SEQ ID NO: 4)

DETAILED DESCRIPTION

Figure 5:
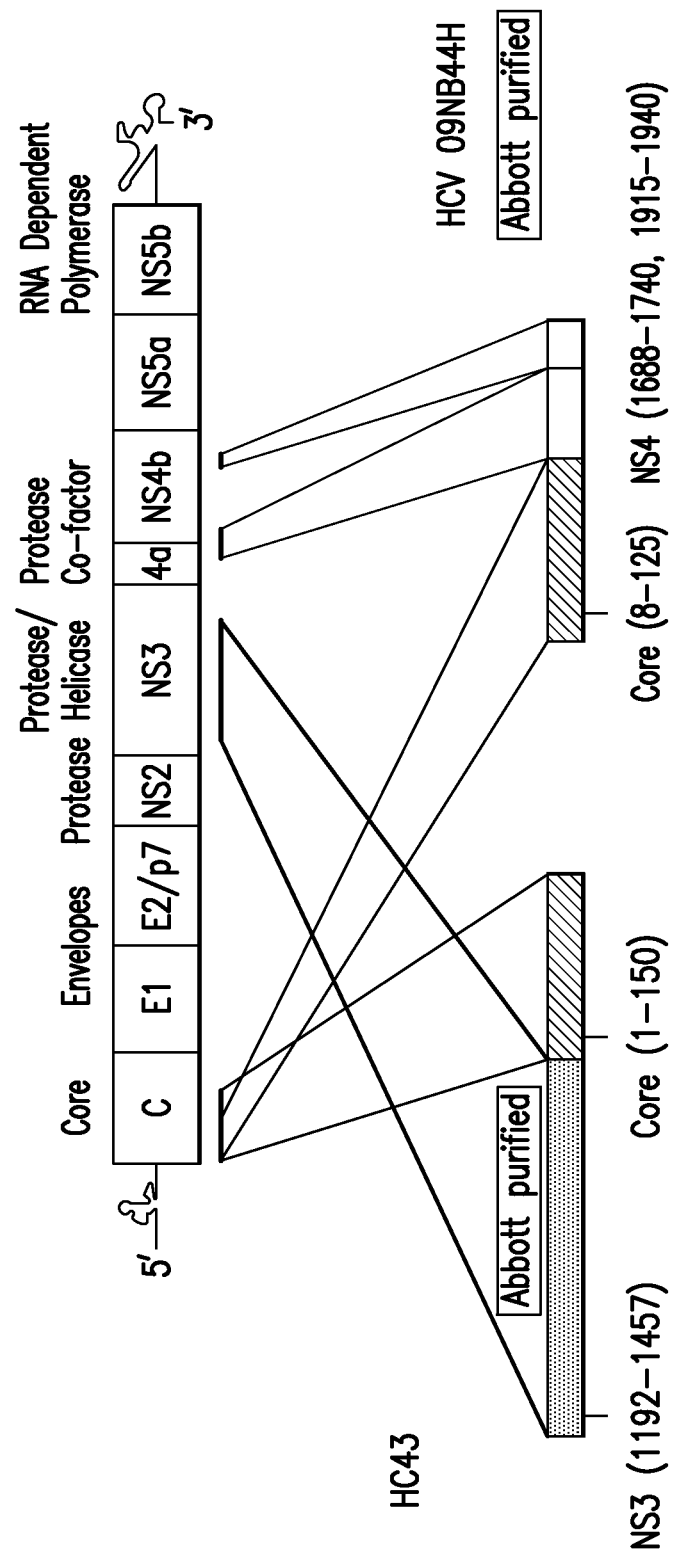
FIG. 5 is a diagram of the construction of 9NB44H and HC43H. The carboxyl-terminal 6×His (SEQ ID NO: 5) is not shown.

The present disclosure is predicated, at least in part, on the discovery that the use of (i) a polypeptide comprising the contiguous amino acids 8-125 (core), 1688-1740 (NS4), and 1915-1940 (NS4) of hepatitis C virus (HCV) in combination with (ii) a polypeptide comprising an epitope that is immunoreactive with an antibody that specifically binds to the NS3 region of HCV, such as an epitope contained within the contiguous amino acids 1192-1457 of HCV, alone or in further combination with an epitope that is immunoreactive with an antibody that specifically binds to the core region of HCV, such as an epitope contained within the contiguous amino acids 1-150 of HCV, in an immunoassay of anti-HCV antibodies can achieve a level of sensitivity that is better than a commercially available immunoassay. The polypeptide of (i) can be advantageously produced in large quantities in bacteria, such as *E. coli*. Preferably, the polypeptides are coated on microparticles, and more preferably, the polypeptides are co-coated on the same microparticles. When the polypeptides are co-coated on the same microparticles, preferably the polypeptides (i) and (ii) are co-coated in a ratio of about 1:2 to about 1:6. When (i) and (ii) are co-coated on the same microparticles in a ratio of about 1:2, preferably the concentration of (i) is at least about 40 μg/mL and the concentration of (ii) is at least about 80 μg/mL. The following terms are relevant to the present disclosure:

(a) "About" refers to approximately a +/−10% variation from the stated value. It is to be understood that such a variation is always included in any given value provided herein, whether or not specific reference is made to it.

(b) "Antibody fragment" and "antibody fragments" refer to a portion of an intact antibody comprising the antigen-binding site or variable region. The portion does not include the constant heavy chain domains (i.e., $C_H2$, $C_H3$ or $C_H4$, depending on the antibody isotype) of the Fc region of the intact antibody. Examples of antibody fragments include, but are not limited to, Fab fragments, Fab' fragments, Fab'-SH fragments, $F(ab')_2$ fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

(c) "Antibody" (Ab) and "antibodies" (Abs) refer to monoclonal antibodies (mAb (singular) or mAbs (plural)), polyclonal antibodies (pAbs (plural)), multispecific antibodies, human antibodies, humanized antibodies (fully or partially humanized; a polypeptide comprising a modified variable region of a human antibody wherein a portion of the variable region has been substituted by the corresponding sequence from a non-human sequence and wherein the modified variable region is linked to at least part of the constant region of a human antibody), animal antibodies (such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies (cAb; a polypeptide comprising all or a part of the heavy and light chain variable regions of an antibody from one host species linked to at least part of the antibody constant regions from another host species), single chain antibodies, single domain antibodies, Fab fragments, F(ab') fragments, Fab'-SH fragments, $F(ab')_2$ fragments, Fd fragments, Fv fragments, single-chain Fv fragments ("scFv"), disulfide-linked Fv fragments ("sdFv"), dAb fragments, diabodies, an isolated complementarity determining region (CDR), and anti-idiotypic ("anti-Id") antibodies, bifunctional or dual-domain antibodies (e.g., dual variable domain antibodies, or DVD-IgGs), and functionally active, epitope-binding fragments (or antigenically reactive fragments) of any of the above. In particular, antibodies include immunoglobulin molecules and immunologically active (or antigenically reactive) fragments of immunoglobulin molecules, namely, molecules that contain an analyte-binding site as further described in (n) herein, and variants as further described in (ac) herein Immunoglobulin molecules can be of any type (for example, IgG, IgE, IgM, IgD, IgA and IgY), class (for example, $IgG_1$, $IgG_2$, $IgG_3$, $IgG_4$, $IgA_1$ and $IgA_2$), or subclass. An antibody, whose affinity (namely, $K_D$, $k_d$ or $k_a$) has been increased or improved via the screening of a combinatory antibody library that has been prepared using bio-display, is referred to as an "affinity maturated antibody." For simplicity sake, an antibody against an analyte is frequently referred to herein as being either an "anti-analyte antibody" or merely an "analyte antibody" (e.g., an anti-HCV antibody or an HCV antibody). A variant of an antibody is as described in (x) herein.

(d) "Component," "components," and "at least one component," refer generally to a capture antibody, a detection or conjugate antibody, a control, a calibrator, a series of calibrators, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Thus, in the context of the present disclosure, "at least one component," "component," and "components" can include a polypeptide as described herein, which is optionally immobilized on a solid support. Some components can be in solution or lyophilized for reconstitution for use in an assay.

(e) "Control" refers to a composition known to not contain anti-HCV antibody ("negative control") or to contain anti-HCV antibody ("positive control"). A positive control can comprise a known concentration of anti-HCV antibody. "Control," "positive control," and "calibrator" may be used interchangeably herein to refer to a composition comprising a known concentration of anti-HCV antibody. A "positive control" can be used to establish assay performance characteristics and is a useful indicator of the integrity of reagents (e.g., analytes).

(f) "Epitope," "epitopes" and "epitopes of interest" refer to a site(s) on any molecule that is recognized and can bind to a complementary site on a specific binding partner, such as an antibody or antigenically reactive fragment thereof. An epitope consists of the precise amino acid residues of a region of an antigen (or fragment thereof) known to bind to the complementary site on the specific binding partner. An antigenic fragment can contain more than one epitope.

(g) "Hepatitis C Virus" or "HCV" has a 9.5 kb positive-sense, single-stranded RNA genome and is a member of the Flaviviridae family of viruses. Based on phylogenetic analysis, at least six distinct, but related, genotypes of HCV have been identified (Simmonds et al., J. Gen. Virol. 74: 2391-2399 (1993)). The virus encodes a single polyprotein having more than 3,000 amino acid residues (Choo et al., Science 244: 359-362 (1989)). The polyprotein is processed co- and post-translationally into both structural and non-structural proteins. The polyprotein is cleaved into the following products: $NH_2$-C-E1-E2-P7-N52-N53-NS4a-NS4b-NS5a-NS5b-COOH. Initial cleavage of the polyprotein is catalyzed by host proteases, which liberate three structural proteins, the N-terminal nucleocapsid protein (called "core" and designated "C") and two envelope glycoproteins "E1" (also known as E) and "E2" (also known as E2/NS1), as well as nonstructural (NS) proteins that contain the viral enzymes. The NS regions are termed NS2, NS3, NS4, NS4a, NS4b, NS5a and NS5b. Genomic sequences of HCV genotypes are known. See, e,g., NC 004102 (genotype 1), NC 009823 (genotype 2), NC 009824 (genotype 3), NC 009825 (genotype 4), NC 009826 (genotype 5), and NC 009827 (genotype 6), which are available from National Center for Biotechnology Information (Bethesda, Md.).

(h) "Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

(i) "Label" and "detectable label" mean a moiety attached to a specific binding partner, such as an antibody or an analyte, to render the reaction between members of a specific binding pair, such as an antibody and an analyte, detectable, and the specific binding partner, e.g., antibody or analyte, so labeled is referred to as "detectably labeled." A label can produce a signal that is detectable by visual or instrumental means. Various labels include signal-producing substances, such as chromogens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety itself may not be detectably labeled but may become detectable upon reaction with yet another moiety. Use of "detectably labeled" is intended to encompass the latter type of detectable labeling.

(j) "Linking sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Exemplary linking sequences include, but are not limited to: (i) Histidine (His) tags, such as a 6×His tag (SEQ ID NO: 5), which contains six histidine residues, are useful as linking sequences to facilitate the isolation and purification of polypeptides and antibodies of interest. (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. (iii) Miscellaneous sequences can be used to link or connect the light and/or heavy chain variable regions of single chain variable region fragments. Examples of other linking sequences can be found in Bird et al., Science 242: 423-426 (1988); Huston et al., PNAS USA 85: 5879-5883 (1988); and McCafferty et al., Nature 348: 552-554 (1990). Linking sequences also can be modified for additional functions, such as attachment of drugs or attachment to solid supports. In the context of the present disclosure, an mAb, for example, can contain a linking sequence, such as a His tag, an enterokinase cleavage site, or both.

(k) "Patient" and "subject" may be used interchangeably herein to refer to an animal, such as a bird (e.g., a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, and a mouse) and a primate (for example, a monkey, a chimpanzee, and a human). Preferably, the patient or subject is a human, such as a human at risk for HCV infection or a human infected with HCV.

(l) "Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (e.g., severity of disease, progression/nonprogression/improvement, etc.). While the present disclosure may provide exemplary predetermined levels, it is well-known that cutoff values may vary depending on the nature of the immunoassay (e.g., antibodies employed, etc.). It further is well within the ordinary skill of one in the art to adapt the disclosure herein for other immunoassays to obtain immunoassay-specific cutoff values for those other immunoassays based on this disclosure. Whereas the precise value of the predetermined cutoff/level may vary between assays, the correlations as described herein should be generally applicable.

(m) "Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (i.e., anti-HCV antibody) entails release of the analyte from any endogenous binding proteins present in the sample. A pretreatment reagent may be homogeneous (not requiring a separation step) or heterogeneous (requiring a separation step). With use of a heterogeneous pretreatment reagent there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

(n) "Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction so as to comprise a "sensitivity panel."

(o) "Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced mAbs, chimeric antibodies, humanized antibodies (fully or partially humanized), multi-specific or multi-valent structures formed from antibody fragments, bifunctional antibodies and other antibodies as described in (c) herein.

(p) "Risk" refers to the possibility or probability of a particular event occurring either presently or at some point in the future. "Risk stratification" refers to an array of known clinical risk factors that allows physicians to classify patients into a low, moderate, high or highest risk of developing a particular disease, disorder or condition.

(q) "Sample," "test sample," and "patient sample" may be used interchangeably herein. The sample, such as a sample of urine, serum, plasma, amniotic fluid, cerebrospinal fluid, placental cells or tissue, endothelial cells, leukocytes, or monocytes, can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art. Preferably, the sample is urine, serum or plasma.

(r) "Series of calibrating compositions" refers to a plurality of compositions comprising a known concentration of anti-HCV antibody, wherein each of the compositions differs from the other compositions in the series by the concentration of anti-HCV antibody.

(s) "Solid phase" refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. The linking agent can, for example, include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. The solid phase can, for example, be plastic, derivatized plastic, magnetic or non-magnetic metal, glass or silicon, including, for example, a test tube, microtiter well, sheet, bead, microparticle, chip, and other configurations known to those of ordinary skill in the art.

(t) "Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes, fragments, and variants (including fragments of variants) thereof, whether isolated or recombinantly produced.

(u) "Specific" and "specificity" in the context of an interaction between members of a specific binding pair (e.g., an antigen (or fragment thereof) and an antibody (or antigenically reactive fragment thereof)) refer to the selective reactivity of the interaction. The phrase "specifically binds to" and analogous phrases refer to the ability of antibodies (or antigenically reactive fragments thereof) to bind specifically to a given antigen (or a fragment thereof) and not bind specifically to other entities.

(v) "Substantially identical" as used herein in relation to a nucleic acid or amino acid sequence indicates that, when optimally aligned, for example using the methods described below, the nucleic acid or amino acid sequence shares at least about 70%, at least about 75%, at least about 80%, at least about 85%, at least about 90%, at least about 95%, at least about 96%, at least about 97%, at least about 98% or at least about 99% sequence identity with a defined second nucleic acid or amino acid sequence (or "reference sequence"). "Substantial identity" may be used to refer to various types and lengths of sequence, such as full-length sequence, epitopes or immunogenic peptides, functional domains, coding and/or regulatory sequences, exons, introns, promoters, and genomic sequences. Percent identity between two amino acid or nucleic acid sequences can be determined in various ways that are within the skill of a worker in the art, for example, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed pp 353-358; BLAST program (Basic Local Alignment Search Tool (Altschul, S. F., W. Gish, et al. (1990) J Mol Biol 215: 403-10), and variations thereof including BLAST-2, BLAST-P, BLAST-N, BLAST-X, WU-BLAST-2, ALIGN, ALIGN-2, CLUSTAL, and Megalign (DNASTAR) software. In addition, those skilled in the art can determine appropriate parameters for measuring alignment, including algorithms needed to achieve maximal alignment over the length of the sequences being compared. In general, for amino acid sequences, the length of comparison sequences will be at least about 10 amino acids. One skilled in the art will understand that the actual length will depend on the overall length of the sequences being compared and may be at least about 20, at least about 30, at least about 40, at least about 50, at least about 60, at least about 70, at least about 80, at least about 90, at least about 100, at least about 110, at least about 120, at least about 130, at least about 140, at least about 150, at least about 200, at least about 250, at least about 300, or at least about 350 amino acids, or it may be the full-length of the amino acid sequence. For nucleic acids, the length of comparison sequences will generally be at least about 25 nucleotides, but may be at least about 50, at least about 100, at least about 125, at least about 150, at least about 200, at least about 250, at least about 300, at least about 350, at least about 400, at least about 450, at least about 500, at least about 550, at least about 600, at least about 650, at least about 700, at least about 800, at least about 900, or at least about 1000 nucleotides, or it may be the full-length of the nucleic acid sequence.

(w) "Tracer" means an analyte or analyte fragment conjugated to a label, wherein the analyte conjugated to the label can effectively compete with the analyte for sites on a specific binding partner for the analyte, such as an antibody specific for the analyte. The tracer can be contacted with the antibody simultaneously with or sequentially to, in either order, the analyte.

(x) "Variant" as used herein means a polypeptide that differs from a given polypeptide (e.g., the polypeptide of SEQ ID NO: 2) in amino acid sequence by the addition (e.g., insertion), deletion, or conservative substitution of amino acids, but that retains the biological activity of the given polypeptide (e.g., a variant of SEQ ID NO: 2 can compete with a polypeptide of SEQ ID NO: 2 for binding to an anti-HCV antibody). A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al., J. Mol. Biol. 157: 105-132 (1982)). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101, which is incorporated herein by reference). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to describe a polypeptide or fragment thereof that has been differentially processed, such as by proteolysis, phosphorylation, or other post-translational modification, yet retains its biological activity or antigen reactivity, e.g., the ability to bind to anti-HCV antibody. Use of "variant" herein is intended to encompass fragments of a variant unless otherwise contradicted by context. The above terminology is provided for the purpose of describing particular embodiments. The terminology is not intended to be limiting.

HCV Polypeptides

An isolated or purified polypeptide comprising, consisting essentially of, or consisting of the contiguous amino acids 1-198 of SEQ ID NO: 2 is provided.

Also provided is an isolated or purified polypeptide comprising, consisting essentially of, or consisting of a contiguous amino acid sequence that is at least about 95% (such as at least about 96%, at least about 97%, at least about 98% or at least about 99%) identical to the contiguous amino acids 1-198 of SEQ ID NO: 2. The polypeptide comprises (i) an epitope that is immunoreactive with an antibody that specifically binds to the core protein of hepatitis C virus (HCV) and (ii) an epitope that is immunoreactive with an antibody that specifically binds to the NS4 region of HCV.

The above polypeptides can be recombinantly produced, or synthesized in accordance with methods known in the art. A combination of chemical synthesis and recombinant production also can be used. Specifically, a polynucleotide sequence encoding SEQ ID NO: 2 can be isolated or synthesized. A polynucleotide sequence encoding a sequence that is at least about 95% identical to SEQ ID NO: 2 can be synthesized. See, e.g., "Recombinant Production" herein, Sambrook et al., Molecular Cloning: A Laboratory Manual, $2^{nd}$ ed., Cold Spring Harbor Laboratory Press, Cold Spring Harbor, N.Y. (1989); Kim et al., Biotech. Bioeng. 66: 180-188 (1999); Kim et al., Biotech. Prog. 16: 385-390 (2000); Noren et al., Science 244: 182-188 (1989)); and Swartz et al., U.S. Pat. No. 7,041,479, which issued May 9, 2006. If recombinantly produced in E. coli, preferably the codons in the donor cDNA are optimized for expression in E. coli (Li et al., Protein Exp. Purif. 32: 110-118 (2003)).

Polypeptides can be isolated or purified from recombinant cell cultures by methods known in the art. Such methods include mechanical cell lysis followed by centrifugation, ammonium sulfate or ethanol precipitation, acid extraction, affinity chromatography (e.g., such as capture on immobilized metal affinity chromatography), anion or cation exchange chromatography, phosphocellulose chromatography, high performance liquid chromatography, hydroxylapatite chromatography, and lectin chromatography. Preferably, the enriched/purified or isolated polypeptide is free from contaminating proteins (e.g., through dialysis), and, where applicable, contains a single, stable conformer. When necessary, conformational homogeneity can be confirmed using ion exchange chromatography, for example. Polypeptides can be refolded in accordance with methods known in the art (e.g., by the addition of a folding enzyme, such as a foldase) to regenerate active conformations after the polypeptides have been denatured during isolation and purification.

Synthetic Production

Once sequenced, polypeptides, such as a polypeptide that specifically binds to anti-HCV antibodies, can be synthesized using methods known in the art, such as, for example, exclusive solid phase synthesis, partial solid phase synthesis, fragment condensation, and classical solution synthesis. See, e.g., Merrifield, J. Am. Chem. Soc. 85: 2149 (1963). On solid phase, the synthesis typically begins from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the tradename BIO-BEADS SX-1 by Bio Rad Laboratories (Richmond, Calif.), and the preparation of the hydroxymethyl resin is described by Bodonszky et al., Chem. Ind. (London) 38: 1597 (1966). The benzhydrylamine (BHA) resin has been described by Pietta and Marshall, Chem. Comm. 650 (1970) and is commercially available from Beckman Instruments, Inc. (Palo Alto, Calif.) in the hydrochloride form. Automated peptide synthesizers are commercially available, as are services that make peptides to order.

Thus, the polypeptides can be prepared by coupling an alpha-amino protected amino acid to the chloromethylated resin with the aid of, for example, cesium bicarbonate catalyst, according to the method described by Gisin, Helv. Chim. Acta. 56: 1467 (1973). After the initial coupling, the alpha-amino protecting group is removed by a choice of reagents including trifluoroacetic acid (TFA) or hydrochloric acid (HCl) solutions in organic solvents at room temperature.

Suitable alpha-amino protecting groups include those known to be useful in the art of stepwise synthesis of peptides. Examples of alpha-amino protecting groups are: acyl type protecting groups (e.g., formyl, trifluoroacetyl, and acetyl), aromatic urethane type protecting groups (e.g., benzyloxycarbonyl (Cbz) and substituted Cbz), aliphatic urethane protecting groups (e.g., t-butyloxycarbonyl (Boc), isopropyloxycarbonyl, and cyclohexyloxycarbonyl), and alkyl type protecting groups (e.g., benzyl and triphenylmethyl). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride and dimethyl formamide (DMF) mixtures.

After the desired amino acid sequence has been completed, the desired peptide is decoupled from the resin support by treatment with a reagent, such as TFA or hydrogen fluoride (HF), which not only cleaves the peptide from the resin, but also cleaves all remaining side chain protecting groups. When the chloromethylated resin is used, HF treatment results in the formation of the free peptide acids. When the benzhydrylamine resin is used, HF treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These and other solid phase peptide synthesis procedures are well-known in the art. Such procedures are also described by Stewart and Young in Solid Phase Peptide Syntheses (2nd Ed., Pierce Chemical Company, 1984).
Recombinant Production A polypeptide, such as a polypeptide that specifically binds to anti-HCV antibodies, can be recombinantly produced using methods known in the art. For example, an isolated nucleic acid comprising a nucleotide sequence encoding the polypeptide can be expressed in a host cell, and the polypeptide can be isolated. The isolated or purified nucleic acid encoding a polypeptide can comprise, consist essentially of, or consist of the contiguous amino acids 1-198 of SEQ ID NO: 2. The isolated or purified nucleic acid can be, and preferably is, contained within a vector. The isolated or purified nucleic acid can comprise, consist essentially of, or consist of nucleotides 1-594 of SEQ ID NO: 1. The isolated nucleic acid can be synthesized with an oligonucleotide synthesizer, for example. One of ordinary skill in the art will readily appreciate that, due to the degeneracy of the genetic code, more than one nucleotide sequence can encode a given amino acid sequence. In this regard, the isolated or purified nucleic acid encoding a polypeptide can comprise, consist essentially of, or consist of a contiguous amino acid sequence that is at least about 95% (such as at least about 96%, at least about 97%, at least about 98% or at least about 99%) identical to the contiguous amino acids 1-198 of SEQ ID NO: 2, provided that the variant polypeptide comprises (i) an epitope that is immunoreactive with an antibody that specifically binds to the core protein of HCV and (ii) an epitope that is immunoreactive with an antibody that specifically binds to the NS4 region of HCV. Preferably, the variant polypeptide as expressed competes with the polypeptide comprising the contiguous amino acids 1-198 of SEQ ID NO: 2 for binding to the anti-HCV antibody. Codons, which are favored by a given host cell, preferably are selected for recombinant production. A nucleotide sequence encoding amino acids 1-198 of SEQ ID NO: 2 can be combined with other nucleotide sequences using polymerase chain reaction (PCR), ligation, or ligation chain reaction (LCR) to encode the desired polypeptide. The individual oligonucleotides typically contain 5' or 3' overhangs for complementary assembly. Once assembled, the nucleotide sequence encoding the polypeptide can be inserted into a vector, operably linked to control sequences as necessary for expression in a given host cell, and introduced (such as by transformation or transfection) into a host cell. The nucleotide sequence can be further manipulated (for example, linked to one or more nucleotide sequences encoding additional immunoglobulin domains, such as additional constant regions) and/or expressed in a host cell.

Although not all vectors and expression control sequences may function equally well to express a polynucleotide sequence of interest and not all hosts function equally well with the same expression system, it is believed that those skilled in the art will be able to make a selection among these vectors, expression control sequences, optimized codons, and hosts for use in the present disclosure without any undue experimentation. For example, in selecting a vector, the host must be considered because the vector must be able to replicate in it or be able to integrate into the chromosome. The vector's copy number, the ability to control that copy number, and the expression of any other proteins encoded by the vector, such as antibiotic markers, should also be considered. In selecting an expression control sequence, a variety of factors also can be considered. These include, but are not limited to, the relative strength of the sequence, its controllability, and its compatibility with the nucleotide sequence encoding the polypeptide, particularly with regard to potential secondary structures. Hosts should be selected by consideration of their compatibility with the chosen vector, their codon usage, their secretion characteristics, their ability to fold the polypeptide correctly, their fermentation or culture requirements, their ability (or lack thereof) to glycosylate the protein, and the ease of purification of the products encoded by the nucleotide sequence, etc.

The recombinant vector can be an autonomously replicating vector, namely, a vector existing as an extrachromosomal entity, the replication of which is independent of chromosomal replication (such as a plasmid). Alternatively, the vector can be one which, when introduced into a host cell, is integrated into the host cell genome and replicated together with the chromosome(s) into which it has been integrated.

In the context of the present disclosure, a vector comprising an isolated or purified nucleic acid encoding a polypeptide comprising, consisting essentially of, or consisting of the contiguous amino acids 1-198 of SEQ ID NO: 2 is provided. The nucleic acid can comprise nucleotides 1-594 of SEQ ID NO: 1. Also provided is a vector comprising an isolated or purified nucleic acid encoding a polypeptide comprising, consisting essentially of, or consisting of a contiguous amino acid sequence that is at least about 95% identical to the contiguous amino acids 1-198 of SEQ ID NO: 2, wherein the polypeptide comprises (i) an epitope that is immunoreactive with an antibody that specifically binds to the core protein of HCV and (ii) an epitope that is immunoreactive with an antibody that specifically binds to the NS4 region of HCV.

The vector is preferably an expression vector in which the polynucleotide sequence encoding the polypeptide is operably linked to additional segments required for transcription of the polynucleotide sequence. The vector is typically derived from plasmid or viral DNA. A number of suitable expression vectors for expression in the host cells mentioned herein are commercially available or described in the literature. Examples of suitable expression vectors for use in the context of the present disclosure include, but are not limited to, pTrc99A, pBAD24, vectors containing a Coil origin of replication and its derivatives, pUC, pBluescript, pGEM, and pTZ vectors. Useful expression vectors for eukaryotic hosts, include, but are not limited to, vectors comprising expression control sequences from SV40, bovine papilloma virus, adenovirus and cytomegalovirus. Specific vectors include pcDNA3.1 (+)\Hyg (Invitrogen Corp., Carlsbad, Calif.) and pCI-neo (Stratagene, La Jolla, Calif.). Examples of expression vectors for use in yeast cells include, but are not limited to, the 2µ plasmid and derivatives thereof, the POT1 vector (see, e.g., U.S. Pat. No. 4,931,373), the pJSO37 vector (described in Okkels, Ann. New York Acad. Sci. 782: 202-207 (1996)) and pPICZ A, B or C (Invitrogen). Examples of expression vectors for use in insect cells include, but are not limited to, pVL941, pBG311 (Cate et al., Cell 45: 685-698 (1986)), and pBluebac 4.5 and pMelbac (both of which are available from Invitrogen).

Other vectors that can be used allow the nucleotide sequence encoding the polypeptide to be amplified in copy number. Such amplifiable vectors are well-known in the art. These vectors include, but are not limited to, those vectors that can be amplified by dihydrofolate reductase (DHFR) amplification (see, for example, Kaufman, U.S. Pat. No. 4,470,461; and Kaufman et al., Mol. Cell. Biol. 2: 1304-1319 (1982)) and glutamine synthetase (GS) amplification (see, for example, U.S. Pat. No. 5,122,464 and European Pat. App. Pub. No. 0 338 841).

The recombinant vector can further comprise a nucleotide sequence enabling the vector to replicate in the host cell in question. An example of such a sequence for use in a mammalian host cell is the SV40 origin of replication. Suitable sequences enabling the vector to replicate in a yeast cell are the yeast plasmid 2µ replication genes REP 1-3 and origin of replication.

The vector can also comprise a selectable marker, namely, a gene or polynucleotide, the product of which complements a defect in the host cell, such as the gene coding for DHFR or the *Schizosaccharomyces pombe* TPI gene (see, e.g., Russell, Gene 40: 125-130 (1985)), or one which confers resistance to a drug, such as ampicillin, kanamycin, tetracycline, chloramphenicol, neomycin, hygromycin or methotrexate. For filamentous fungi, selectable markers include, but are not limited to, amdS, pyrG, arcB, niaD and sC.

Also present in the vector are "control sequences," which are any components that are necessary or advantageous for the expression of the polypeptide. Each control sequence can be native or foreign to the nucleotide sequence encoding the polypeptide. Such control sequences include, but are not limited to, a leader, a polyadenylation sequence, a propeptide sequence, a promoter, an enhancer or an upstream activating sequence, a signal peptide sequence, and a transcription terminator. At a minimum, the control sequences include at least one promoter operably linked to the polynucleotide sequence encoding the polypeptide.

By "operably linked" is meant the covalent joining of two or more nucleotide sequences, by means of enzymatic ligation or otherwise, in a configuration relative to one another such that the normal function of the sequences can be performed. For example, a nucleotide sequence encoding a presequence or secretory leader is operably linked to a nucleotide sequence for a polypeptide if it is expressed as a preprotein that participates in the secretion of the polypeptide; a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in the same reading frame. Linking is accomplished by ligation at convenient restriction sites. If such sites do not exist, then synthetic oligonucleotide adaptors or linkers can be used, in conjunction with standard recombinant DNA methods.

A wide variety of expression control sequences can be used in the context of the present disclosure. Such useful expression control sequences include the expression control sequences associated with structural genes of the foregoing expression vectors as well as any sequence known to control the expression of genes of prokaryotic or eukaryotic cells or their viruses, and various combinations thereof. Examples of suitable control sequences for use in bacteria, such as *E. coli*, include, but are not limited to, Trc, Tac, T5, T7, and $P_{Lambda}$ (pL) promoters. In a preferred embodiment, the promoter is pL. Examples of suitable control sequences for directing transcription in mammalian cells include the early and late promoters of SV40 and adenovirus, for example, the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus E1b region polyadenylation signals and the Kozak consensus sequence (Kozak, J. Mol. Biol. 196: 947-50 (1987)).

In order to improve expression in mammalian cells a synthetic intron can be inserted in the 5' untranslated region of a polynucleotide sequence encoding the antibody or a fragment thereof. An example of a synthetic intron is the synthetic intron from the plasmid pCI-Neo (available from Promega Corporation, Madison, Wis.).

Examples of suitable control sequences for directing transcription in insect cells include, but are not limited to, the polyhedrin promoter, the P10 promoter, the baculovirus immediate early gene 1 promoter, the baculovirus 39K delayed-early gene promoter, and the SV40 polyadenylation sequence.

Examples of suitable control sequences for use in yeast host cells include the promoters of the yeast α-mating system, the yeast triose phosphate isomerase (TPI) promoter, promoters from yeast glycolytic genes or alcohol dehydrogenase genes, the ADH2-4-c promoter and the inducible GAL promoter.

Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulas* glucoamylase, *A. nidulans* acetamidase, *Rhizomucor miehei* aspartic proteinase or lipase, the TPI1 terminator, and the ADH3 terminator.

The polynucleotide sequence encoding the polypeptide of interest may or may not also include a polynucleotide sequence that encodes a signal peptide. The signal peptide is present when the polypeptide is to be secreted from the cells in which it is expressed. Such signal peptide, if present, should be one recognized by the cell chosen for expression of the polypeptide. The signal peptide can be homologous or heterologous to the polypeptide or can be homologous or heterologous to the host cell, i.e., a signal peptide normally expressed from the host cell or one which is not normally expressed from the host cell. Accordingly, the signal peptide can be prokaryotic, for example, derived from a bacterium, or eukaryotic, for example, derived from a mammalian, insect, filamentous fungal, or yeast cell.

The presence or absence of a signal peptide will, for example, depend on the expression host cell used for the production of the polypeptide. For use in filamentous fungi, the signal peptide can conveniently be derived from a gene encoding an *Aspergillus* sp. amylase or glucoamylase, a gene encoding a *Rhizomucor miehei* lipase or protease or a *Humicola lanuginosa* lipase. For use in insect cells, the signal peptide can be derived from an insect gene (see, e.g., Int'l Pat. App. Pub. No. WO 90/05783), such as the lepidopteran *Manduca sexta* adipokinetic hormone precursor (see, e.g., U.S. Pat. No. 5,023,328), the honeybee melittin (Invitrogen), ecdysteroid UDP glucosyltransferase (egt) (Murphy et al., Protein Expression and Purification 4: 349-357 (1993), or human pancreatic lipase (hpl) (Methods in Enzymology 284: 262-272 (1997)).

Specific examples of signal peptides for use in mammalian cells include murine Ig kappa light chain signal peptide (Coloma, J. Imm. Methods 152: 89-104 (1992)). Suitable signal peptides for use in yeast cells include the α-factor signal peptide from *S. cerevisiae* (see, e.g., U.S. Pat. No. 4,870,008), the signal peptide of mouse salivary amylase (see, e.g., Hagenbuchle et al., Nature 289: 643-646 (1981)), a modified carboxypeptidase signal peptide (see, e.g., Valls et al., Cell 48: 887-897 (1987)), the yeast BAR1 signal peptide (see, e.g., Int'l Pat. App. Pub. No. WO 87/02670), and the yeast aspartic protease 3 (YAP3) signal peptide (see, e.g., Egel-Mitani et al., Yeast 6: 127-137 (1990)).

In view of the foregoing, also provided is a host cell comprising an isolated or purified nucleic acid as described above. Any suitable host can be used to produce the polypeptide, including bacteria, fungi (including yeasts), plant, insect, mammal or other appropriate animal cells or cell lines, as well as transgenic animals or plants. Examples of bacterial host cells include, but are not limited to, gram-positive bacteria, such as strains of *Bacillus*, for example, *B. brevis* or *B. subtilis*, *Pseudomonas* or *Streptomyces*, or gram-negative bacteria, such as strains of *E. coli*. Preferably, the host cell is *E. coli*, in which case the preferred promoter is pL. The introduction of a vector into a bacterial host cell can, for instance, be effected by protoplast transformation (see, for example, Chang et al., Molec. Gen. Genet. 168: 111-115 (1979)), using competent cells (see, for example, Young et al., J. of Bacteriology 81: 823-829 (1961), or Dubnau et al., J. of Molec. Biol. 56: 209-221 (1971)), electroporation (see, for example, Shigekawa et al., Biotechniques 6: 742-751 (1988)), or conjugation (see, for example, Koehler et al., J. of Bacteriology 169: 5771-5278 (1987)).

Examples of suitable filamentous fungal host cells include, but are not limited to, strains of *Aspergillus*, for example, *A. oryzae, A. niger,* or *A. nidulans, Fusarium* or *Trichoderma*. Fungal cells can be transformed by a process involving protoplast formation, transformation of the protoplasts, and regeneration of the cell wall using techniques known to those ordinarily skilled in the art. Suitable procedures for transformation of *Aspergillus* host cells are described in European Pat. App. Pub. No. 238 023 and U.S. Pat. No. 5,679,543. Suitable methods for transforming *Fusarium* species are described by Malardier et al., Gene 78: 147-156 (1989), and Int'l Pat. App. Pub. No. WO 96/00787. Yeast can be transformed using the procedures described by Becker and Guarente, In Abelson, J. N. and Simon, M. I., editors, Guide to Yeast Genetics and Molecular Biology, Methods in Enzymology 194: 182-187, Academic Press, Inc., New York; Ito et al, J. of Bacteriology 153: 163 (1983); and Hinnen et al., PNAS USA 75: 1920 (1978).

Examples of suitable yeast host cells include strains of *Saccharomyces*, for example, *S. cerevisiae, Schizosaccharomyces, Klyveromyces, Pichia*, such as *P. pastoris* or *P. methanolica, Hansenula*, such as *H. polymorpha* or *yarrowia*. Methods for transforming yeast cells with heterologous polynucleotides and producing heterologous polypeptides therefrom are disclosed by Clontech Laboratories, Inc, Palo Alto, Calif., USA (in the product protocol for the Yeastmaker™ Yeast Tranformation System Kit), and by Reeves et al., FEMS Microbiology Letters 99: 193-198 (1992), Manivasakam et al., Nucleic Acids Research 21: 4414-4415 (1993), and Ganeva et al., FEMS Microbiology Letters 121: 159-164 (1994).

Examples of suitable insect host cells include, but are not limited to, a Lepidoptora cell line, such as *Spodoptera frugiperda* (Sf9 or Sf21) or *Trichoplusia ni* cells (High Five) (see, e.g., U.S. Pat. No. 5,077,214). Transformation of insect cells and production of heterologous polypeptides are well-known to those skilled in the art.

Examples of suitable mammalian host cells include Chinese hamster ovary (CHO) cell lines, simian (e.g., Green Monkey) cell lines (COS), mouse cells (for example, NS/O), baby hamster kidney (BHK) cell lines, human cells (such as human embryonic kidney (HEK) cells (e.g., HEK 293 cells (A.T.C.C. Accession No. CRL-1573))), myeloma cells that do not otherwise produce immunoglobulin protein, and plant cells in tissue culture. Preferably, the mammalian host cells are CHO cell lines and HEK 293 cell lines. Another preferred host cell is the B3.2 cell line (e.g., Abbott Laboratories, Abbott Bioresearch Center), or another dihydrofolate reductase deficient (DHFR$^-$) CHO cell line (e.g., available from Invitrogen).

Methods for introducing exogenous polynucleotides into mammalian host cells include calcium phosphate-mediated transfection, electroporation, DEAE-dextran mediated transfection, liposome-mediated transfection, viral vectors and the transfection method described by Life Technologies Ltd, Paisley, UK using Lipofectamine™ 2000. These methods are well-known in the art and are described, for example, by Ausbel et al. (eds.), Current Protocols in Molecular Biology, John Wiley & Sons, New York, USA (1996). The cultivation of mammalian cells is conducted according to established methods, e.g., as disclosed in Jenkins, Ed., Animal Cell Biotechnology, Methods and Protocols, Human Press Inc. Totowa, N.J., USA (1999), and Harrison and Rae, General Techniques of Cell Culture, Cambridge University Press (1997).

In the production methods, cells are cultivated in a nutrient medium suitable for production of the polypeptide using methods known in the art. For example, cells are cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or can be prepared according to published compositions (e.g., in catalogues of the American Type Culture Collection). If the polypeptide is secreted into the nutrient medium, it can be recovered directly from the medium. If the polypeptide is not secreted, it can be recovered from cell lysates.

The resulting polypeptide can be recovered by methods known in the art. For example, the polypeptide can be recovered from the nutrient medium by conventional procedures including, but not limited to, centrifugation, filtration, extraction, spray drying, evaporation, or precipitation.

The polypeptide can be purified by a variety of procedures known in the art including, but not limited to, chromatography (such as, but not limited to, ion exchange, affinity, hydrophobic, chromatofocusing, and size exclusion), electrophoretic procedures (such as, but not limited to, preparative isoelectric focusing), differential solubility (such as, but not limited to, ammonium sulfate precipitation), SDS-PAGE, or extraction (see, for example, Janson and Ryden, editors, Protein Purification, VCH Publishers, New York (1989)).

Anti-HCV antibodies and fragments of anti-HCV antibodies (and variants thereof) can be used in the context of the present disclosure. For example, the antibody fragment can include, but is not limited to, a Fab, a Fab', a Fab'-SH fragment, a di-sulfide linked Fv, a single chain Fv (scFv) and a F(ab')$_2$ fragment. Various techniques are known to those skilled in the art for the production of antibody fragments. Such fragments can be derived via proteolytic digestion of intact antibodies (see, for example, Morimoto et al., J. Biochem. Biophys. Methods 24: 107-117 (1992); and Brennan et al., Science 229: 81 (1985)). For example, Fab fragments can be prepared from whole antibodies by papain digestion, whereas F(ab')$_2$ fragments can be prepared from whole antibodies by pepsin digestion. Such fragments also can be produced directly by recombinant host cells. For example, Fab'-SH fragments can be directly recovered from E. coli and chemically coupled to form F(ab')$_2$ fragments (see, e.g., Carter et al., Bio/Technology 10: 163-167 (1992)). In another embodiment, the F(ab')$_2$ is formed using the leucine zipper GCN4 to promote assembly of the F(ab')$_2$ molecule. Alternatively, Fv, Fab or F(ab')$_2$ fragments can be isolated directly from recombinant host cell culture. Single chain variable region fragments (scFv) are made by linking light and/or heavy chain variable regions by using a short linking peptide or sequence (see, e.g., Bird et al., Science 242: 423-426 (1998)).

The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art. Moreover, other forms of single-chain antibodies, such as diabodies, are also contemplated by the present disclosure. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites (see, for example, Holliger et al., PNAS USA 90: 6444-6448 (1993); and Poljak et al., Structure 2: 1121-1123 (1994)).

The antibody and antigenically reactive fragment thereof have a variety of uses. In one aspect, the antibody (or a fragment thereof) can be used as one or more immunodiagnostic reagents. For example, the antibodies of the present disclosure can be used as one or more immunodiagnostic reagents in one or more methods for detecting the presence, amount or concentration of anti-HCV antibodies in a test sample. More specifically, a detectably labeled anti-IgG antibody, a detectably labeled anti-IgM antibody, and fragments and variants thereof, can be used to detect any anti-HCV antibody that may be present in a test sample.

Antibody Production

Antibodies to HCV (or a fragment thereof, a variant thereof, or a fragment of a variant thereof) for use in the context of the present disclosure can be made using a variety of different techniques known in the art. For example, polyclonal and monoclonal antibodies can be raised by immunizing a suitable subject (such as, but not limited to, a rabbit, goat, mouse or other mammal) with an immunogenic preparation which contains a suitable immunogen. The immunogen can be enriched/purified and isolated from a cell that produces it using affinity chromatography, immunoprecipitation or other techniques which are well known in the art, can be used as an immunogen. Alternatively, immunogen can be prepared using chemical synthesis using routine techniques known in the art (such as, but not limited to, a synthesizer). The antibodies raised in the subject can then be screened to determine if the antibodies bind to the immunogen (or a fragment thereof, a variant thereof, or a fragment of a variant thereof).

The unit dose of immunogen (namely, the purified protein, tumor cell expressing the protein, or recombinantly expressed immunogen (or a fragment thereof, a variant thereof, or a fragment of a variant thereof) and the immunization regimen will depend upon the subject to be immunized, its immune status, and the body weight of the subject. To enhance an immune response in the subject, an immunogen can be administered with an adjuvant, such as Freund's complete or incomplete adjuvant.

Immunization of a subject with an immunogen as described above induces a polyclonal antibody response. The antibody titer in the immunized subject can be monitored over time by standard techniques such as an ELISA using an immobilized antigen.

Other methods of raising antibodies include using transgenic mice, which express human immunoglobin genes (see, for example, Int'l Pat. App. Pub. Nos. WO 91/00906, WO 91/10741, and WO 92/03918). Alternatively, human monoclonal antibodies can be produced by introducing an antigen into immune-deficient mice that have been engrafted with human antibody-producing cells or tissues (for example, human bone marrow cells, peripheral blood lymphocytes (PBL), human fetal lymph node tissue, or hematopoietic stem cells). Such methods include raising antibodies in SCID-hu mice (see, for example, Int'l Pat. App. Pub. No. WO 93/05796; U.S. Pat. No. 5,411,749; or McCune et al., Science 241: 1632-1639 (1988)) or Rag-1/Rag-2 deficient mice. Human antibody-immune deficient mice are also commercially available. For example, Rag-2 deficient mice are available from Taconic Farms (Germantown, N.Y.).

Monoclonal antibodies can be generated by immunizing a subject with an immunogen. At the appropriate time after immunization, for example, when the antibody titers are at a sufficiently high level, antibody producing cells can be harvested from an immunized animal and used to prepare monoclonal antibodies using standard techniques. For example, the antibody producing cells can be fused by standard somatic cell fusion procedures with immortalizing cells such as myeloma cells to yield hybridoma cells. Such techniques are well-known in the art, and include, for example, the hybridoma technique as originally developed by Kohler and Milstein, Nature 256: 495-497 (1975)), the human B cell hybridoma technique (Kozbar et al., Immunology Today 4: 72 (1983)), and the EBV-hybridoma technique to produce human monoclonal antibodies (Cole et al., Monoclonal Antibodies and Cancer Therapy, Alan R. Liss, Inc. pp. 77-96 (1985)). The technology for producing monoclonal antibody hybridomas is well-known to those skilled in the art.

Monoclonal antibodies also can be made by harvesting antibody producing cells, for example, splenocytes, from transgenic mice expressing human immunoglobulin genes and which have been immunized with the immunogen. The splenocytes can be immortalized through fusion with human myelomas or through transformation with Epstein-Barr virus (EBV). These hybridomas can be made using human B cell- or EBV-hybridoma techniques described in the art (See, for example, Boyle et al., European Pat. Pub. No. 0 614 984).

Hybridoma cells producing a monoclonal antibody which specifically binds to the immunogen are detected by screening the hybridoma culture supernatants by, for example, screening to select antibodies that specifically bind to the immobilized immunogen (or fragment thereof), or by testing the antibodies as described herein to determine if the antibodies have the desired characteristics, namely, the ability to bind to immunogen (or fragment thereof). After hybridoma cells are identified that produce antibodies of the desired specificity, the clones may be subcloned, e.g., by limiting dilution procedures, for example the procedure described by Wands et al. (Gastroenterology 80: 225-232 (1981)), and grown by standard methods.

Hybridoma cells that produce monoclonal antibodies that test positive in the screening assays described herein can be cultured in a nutrient medium under conditions and for a time sufficient to allow the hybridoma cells to secrete the monoclonal antibodies into the culture medium, to thereby produce whole antibodies. Tissue culture techniques and culture media suitable for hybridoma cells are generally described in the art (See, for example, R. H. Kenneth, in Monoclonal Antibodies: A New Dimension In Biological Analyses, Plenum Publishing Corp., New York, N.Y. (1980)). Conditioned hybridoma culture supernatant containing the antibody can then be collected. The monoclonal antibodies secreted by the subclones optionally can be isolated from the culture medium by conventional immunoglobulin purification procedures such as, for example, protein A chromatography, hydroxylapatite chromatography, gel electrophoresis, dialysis, or affinity chromatography.

Monoclonal antibodies can be engineered by constructing a recombinant combinatorial immunoglobulin library and screening the library with the immunogen or a fragment thereof. Kits for generating and screening phage display libraries are commercially available (See, for example, the Pharmacia Recombinant Phage Antibody System, Catalog No. 27-9400-01; and the Stratagene SurfZAP Phage Display Kit, Catalog No. 240612). Likewise, yeast display vectors are known in the art and are commercially available (for example, pYD1 available from Invitrogen). Briefly, the antibody library is screened to identify and isolate phages or yeast cells that express an antibody that specifically binds to the immunogen or a fragment thereof. Preferably, the primary screening of the library involves screening with an immobilized immunogen or a fragment thereof.

Following screening, the display phage or yeast is isolated and the polynucleotide encoding the selected antibody can be recovered from the display phage or yeast (for example, from the phage or yeast genome) and subcloned into other expression vectors (e.g., into *Saccharomyces cerevesiae* cells, for example EBY100 cells (Invitrogen)) by well-known recombinant DNA techniques. The polynucleotide can be further manipulated (for example, linked to nucleic acid encoding additional immunoglobulin domains, such as additional constant regions) and/or expressed in a host cell.

Once a monoclonal antibody that specifically binds to HCV is obtained in accordance with methods described above, it can be sequenced in accordance with methods known in the art. The antibody then can be made using recombinant DNA technology, chemical synthesis, or a combination of chemical synthesis and recombinant DNA technology as described above.

Furthermore, in some aspects of the disclosure as described herein, it may be possible to employ commercially available anti-HCV antibodies, anti-IgG antibodies, and anti-IgM antibodies or methods for production of anti-HCV antibodies, anti-IgG antibodies, and anti-IgM antibodies as described in the literature. Commercially available antibodies include those available from Abnova (Walnut, Calif., and Taiwan) and GenWay Biotech, Inc. (San Diego, Calif.). See, also, European Pat. App. EP2099825 A2 regarding the preparation of anti-HCV antibodies.

Immunodiagnostic Reagent

Further provided is an immunodiagnostic reagent comprising (i) an above-described isolated or purified polypeptide and (ii) an isolated or purified polypeptide comprising an epitope that is immunoreactive with an antibody that specifically binds to the NS3 region of HCV. The isolated or purified polypeptide comprising an epitope that is immunoreactive with an antibody that specifically binds to the NS3 region of HCV can comprise the contiguous amino acids 1192-1457 of HCV. The isolated or purified polypeptide, which comprises an epitope that is immunoreactive with an antibody that specifically binds to the NS3 region of HCV, can further comprise an epitope that is immunoreactive with an antibody that specifically binds to the core region of HCV. The isolated or purified polypeptide, which comprises (i) an epitope that is immunoreactive with an antibody that specifically binds to the NS3 region of HCV and (ii) an epitope that is immunoreactive with an antibody that specifically binds to the core region of HCV, can comprise the contiguous amino acids 1192-1457 and 1-150 of HCV. The polypeptides of which the immunodiagnostic reagent is comprised can be coated on microparticles. In this regard, the polypeptides of which the immunodiagnostic reagent is comprised can be co-coated on the same microparticles. When the polypeptides are co-coated on the same microparticles, preferably the polypeptides (i) and (ii) are co-coated in a ratio of about 1:2 to about 1:6, wherein, when (i) and (ii) are co-coated on the same microparticles in a ratio of about 1:2, the concentration of (i) is at least about 40 µg/mL and the concentration of (ii) is at least about 80 µg/mL.

Kit

Still further provided is a kit comprising an immunodiagnostic reagent as described above and instructions for the use of the immunodiagnostic reagent in the immunoassay of anti-HCV antibodies. For example, the kit can comprise instructions for assaying the test sample for anti-HCV antibody by immunoassay, e.g., chemiluminescent microparticle immunoassay. The instructions can be in paper form or computer-readable form, such as a disk, CD, DVD, or the like. Alternatively or additionally, the kit can comprise a calibrator or control, e.g., purified, and optionally lyophilized, anti-HCV antibody, and/or at least one container (e.g., tube, microtiter plates or strips, which can be already coated with an immunodiagnostic reagent) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve or a reference standard for purposes of quantifying anti-HCV antibody.

Any antibodies, which are provided in the kit, such as anti-IgG antibodies and anti-IgM antibodies, can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes or reagents for detecting the analyte. The antibodies, calibrators and/or controls can be provided in separate containers or pre-dispensed into an appropriate assay format, for example, into microtiter plates.

Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. If desired, the kit can contain a solid phase, such as a magnetic particle, bead, test tube, microtiter plate, cuvette, membrane, scaffolding molecule, film, filter paper, disc or chip.

Method of Determining the Presence, Amount or Concentration of anti-HCV Antibodies in a Test Sample The present disclosure provides a method for determining the presence, amount or concentration of anti-HCV antibodies in a test sample. Any suitable assay as is known in the art can be used in the method. Examples include, but are not limited to, immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)), competitive inhibition immunoassay (e.g., forward and reverse), fluorescence polarization immunoassay (FPIA), enzyme multiplied immunoassay technique (EMIT), bioluminescence resonance energy transfer (BRET), and homogeneous chemiluminescent assay, etc. In a SELDI-based immunoassay, a capture reagent that specifically binds anti-HCV-antibody is attached to the surface of a mass spectrometry probe, such as a pre-activated protein chip array. The anti-HCV antibody is then specifically captured on the biochip, and the captured anti-HCV antibody is detected by mass spectrometry. Alternatively, the anti-HCV antibody can be eluted from the capture reagent and detected by traditional MALDI (matrix-assisted laser desorption/ionization) or by SELDI. A chemiluminescent microparticle immunoassay, in particular one employing the ARCHITECT® automated analyzer (Abbott Laboratories, Abbott Park, Ill.), is an example of a preferred immunoassay. An agglutination assay, such as a passive hemagglutination assay, also can be used. In an agglutination assay an antigen-antibody reaction is detected by agglutination or clumping. In a passive hemagglutination assay, erythrocytes are coated with the antigen and the coated erythrocytes are used in the agglutination assay.

Methods well-known in the art for collecting, handling and processing urine, blood, serum and plasma, and other body fluids, are used in the practice of the present disclosure, for instance, when the polypeptides according to the present disclosure are employed as immunodiagnostic reagents and/or in an anti-HCV antibody immunoassay kit. The test sample can comprise further moieties in addition to the polypeptide of interest, such as antibodies, antigens, haptens, hormones, drugs, enzymes, receptors, proteins, peptides, polypeptides, oligonucleotides or polynucleotides. For example, the sample can be a whole blood sample obtained from a subject. It can be necessary or desired that a test sample, particularly whole blood, be treated prior to immunoassay as described herein, e.g., with a pretreatment reagent. Even in cases where pretreatment is not necessary (e.g., most urine samples), pretreatment optionally can be done for mere convenience (e.g., as part of a regimen on a commercial platform).

The pretreatment reagent can be any reagent appropriate for use with the immunoassay and kits of the invention. The pretreatment optionally comprises: (a) one or more solvents (e.g., methanol and ethylene glycol) and salt, (b) one or more solvents, salt and detergent, (c) detergent, or (d) detergent and salt. Pretreatment reagents are known in the art, and such pretreatment can be employed, e.g., as used for assays on Abbott TDx, AxSYM®, and ARCHITECT® analyzers (Abbott Laboratories, Abbott Park, Ill.), as described in the literature (see, e.g., Yatscoff et al., Abbott TDx Monoclonal Antibody Assay Evaluated for Measuring Cyclosporine in Whole Blood, Clin. Chem. 36: 1969-1973 (1990), and Wallemacq et al., Evaluation of the New AxSYM Cyclosporine Assay: Comparison with TDx Monoclonal Whole Blood and EMIT Cyclosporine Assays, Clin. Chem. 45: 432-435 (1999)), and/or as commercially available. Additionally, pretreatment can be done as described in Abbott's U.S. Pat. No. 5,135,875, European Pat. Pub. No. 0 471 293, U.S. Provisional Pat. App. 60/878,017, filed Dec. 29, 2006, and U.S. Pat. App. Pub. No. 2008/0020401 (incorporated by reference in its entirety for its teachings regarding pretreatment). The pretreatment reagent can be a heterogeneous agent or a homogeneous agent.

With use of a heterogeneous pretreatment reagent, the pretreatment reagent precipitates analyte binding protein (e.g., protein that can bind to anti-HCV antibody) present in the sample. Such a pretreatment step comprises removing any analyte binding protein by separating from the precipitated analyte binding protein the supernatant of the mixture formed by addition of the pretreatment agent to sample. In such an assay, the supernatant of the mixture absent any binding protein is used in the assay, proceeding directly to the antibody capture step.

With use of a homogeneous pretreatment reagent there is no such separation step. The entire mixture of test sample and pretreatment reagent are contacted with a labeled specific binding partner for anti-HCV antibody, such as a labeled anti-HCV antigen. The pretreatment reagent employed for such an assay typically is diluted in the pretreated test sample mixture, either before or during capture by the first specific binding partner. Despite such dilution, a certain amount of the pretreatment reagent (for example, 5 M methanol and/or 0.6 Methylene glycol) is still present (or remains) in the test sample mixture during capture.

In a heterogeneous format, after the test sample is obtained from a subject, a first mixture is prepared. The mixture contains the test sample being assessed for anti-HCV antibodies and a first specific binding partner, wherein the first specific binding partner and any anti-HCV antibodies contained in the test sample form a first specific binding partner-anti-HCV antibody complex. Preferably, the first specific binding partner is a polypeptide comprising the contiguous amino acids 1-198 of SEQ ID NO: 2 or a polypeptide comprising a contiguous amino acid sequence that is at least about 95% identical (such as at least about 96% identical, at least about 97% identical, at least about 98% identical or at least about 99% identical) to the contiguous amino acids 1-198 of SEQ ID NO: 2 and comprises (i) an epitope that is immunoreactive with an antibody that specifically binds to the core protein of hepatitis C virus (HCV) and (ii) an epitope that is immunoreactive with an antibody that specifically binds to the NS4 region of HCV.

The order in which the test sample and the first specific binding partner are added to form the mixture is not critical. Preferably, the first specific binding partner is immobilized on a solid phase. The solid phase used in the immunoassay (for the first specific binding partner and, optionally, the second specific binding partner) can be any solid phase known in the art, such as, but not limited to, a magnetic particle, a bead, a test tube, a microtiter plate, a cuvette, a membrane, a scaffolding molecule, a film, a filter paper, a disc and a chip.

After the mixture containing the first specific binding partner-anti-HCV antibody complex is formed, any unbound anti-HCV antibody is removed from the complex using any technique known in the art. For example, the unbound anti-HCV antibody can be removed by washing. Desirably, however, the first specific binding partner is present in excess of any anti-HCV antibody present in the test sample, such that all anti-HCV antibody that is present in the test sample is bound by the first specific binding partner.

After any unbound anti-HCV antibody is removed, a second specific binding partner is added to the mixture to form a first specific binding partner-anti-HCV antibody-second specific binding partner complex. The second specific binding partner is preferably a combination of an anti-IgG antibody and an anti-IgM antibody. Moreover, also preferably, the second specific binding partner is labeled with or contains a detectable label as described above.

Any suitable detectable label as is known in the art can be used. For example, the detectable label can be a radioactive label (such as $^3$H, $^{125}$I, $^{35}$S, $^{14}$C, $^{32}$P, and $^{33}$P), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2$^{nd}$ ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

A preferred acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In Luminescence Biotechnology: Instruments and Applications; Dyke, K. V. Ed.; CRC Press:

Boca Raton, pp. 77-105 (2002); Adamczyk et al., Org. Lett. 5: 3779-3782 (2003); and U.S. Pat. Nos. 5,468,646, 5,543, 524 and 5,783,699 (each of which is incorporated herein by reference in its entirety for its teachings regarding same).

Another preferred acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, High Throughput Bioanalytical Sample Preparation. Methods and Automation Strategies, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697, 835, filed Apr. 9, 2007, and published on Oct. 9, 2008, as U.S. Pat. App. Pub. No. 2008/0248493. Acridinium-9-carboxylate aryl esters can be dissolved in any suitable solvent, such as degassed anhydrous N,N-dimethylformamide (DMF) or aqueous sodium cholate.

Chemiluminescent assays can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with an acridinium compound, detectably labeled first specific binding partner-anti-HCV antibody complexes form. Alternatively, if a second specific binding partner is used and the second specific binding partner is detectably labeled with an acridinium compound, detectably labeled first specific binding partner-anti-HCV antibody-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of anti-HCV antibody is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of anti-HCV antibody in the sample can be quantified. Specifically, the amount of anti-HCV antibody in the sample is proportional to the intensity of the signal generated. The amount of anti-HCV antibody present can be quantified by comparing the amount of light generated to a standard curve for anti-HCV antibody or by comparison to a reference standard. The standard curve can be generated using serial dilutions or solutions of known concentrations of anti-HCV antibody by mass spectroscopy, gravimetric methods, and other techniques known in the art.

Anti-HCV antibody immunoassays can be conducted using any suitable format known in the art. Generally speaking, a sample being tested for (for example, suspected of containing) anti-HCV antibodies can be contacted with a capture antigen and at least one detection antibody (which can be a second detection antibody or a third detection antibody), such as labeled anti-IgG and anti-IgM antibodies, either simultaneously or sequentially and in any order. For example, the test sample can be first contacted with at least one capture antigen and then (sequentially) with at least one detection antibody. Alternatively, the test sample can be first contacted with at least one detection antibody and then (sequentially) with at least one capture antibody. In yet another alternative, the test sample can be contacted simultaneously with a capture antigen and a detection antibody.

In the sandwich assay format, a sample suspected of containing anti-HCV antibodies (or a fragment thereof) is first brought into contact with an at least one first capture antigen under conditions that allow the formation of a first capture antigen/anti-HCV antibody complex. If more than one capture antigen is used, multiple first capture antigen/anti-HCV antibody complexes are formed. In a sandwich assay, the antigen(s), preferably, the at least one capture antigen, is/are used in molar excess amounts of the maximum amount of anti-HCV antibodies expected in the test sample. For example, from about 5 µg to about 1 mg of antigen per mL of buffer (e.g., microparticle coating buffer) can be used.

Competitive inhibition immunoassays, which are often used to measure small analytes, comprise sequential and classic formats. In a sequential competitive inhibition immunoassay a capture antigen (i.e., a polypeptide, and preferably a pair of polypeptides, as described herein) to an antibody of interest (i.e., an anti-HCV antibody) is coated onto a well of a microtiter plate. When the sample containing the antibody of interest is added to the well, the antibody of interest binds to the capture antigen. After washing, a known amount of labeled (e.g., biotin or horseradish peroxidase (HRP)) antibody is added to the well. A substrate for an enzymatic label is necessary to generate a signal. An example of a suitable substrate for HRP is 3,3',5,5'-tetramethylbenzidine (TMB). After washing, the signal generated by the labeled antibody is measured and is inversely proportional to the amount of antibody in the sample. In a classic competitive inhibition immunoassay antigen for an antibody of interest is coated onto a well of a microtiter plate. However, unlike the sequential competitive inhibition immunoassay, the sample containing the antibody of interest (i.e., an anti-HCV antibody) and the labeled antibody are added to the well at the same. Any antibody in the sample competes with labeled antibody for binding to the capture antigen. After washing, the signal generated by the labeled analyte is measured and is inversely proportional to the amount of analyte in the sample.

Optionally, prior to contacting the test sample with the at least one capture antigen (for example, the first capture antigen), the at least one capture antigen can be bound to a solid support, which facilitates the separation of the first antigen/anti-HCV antibody complex from the test sample. The substrate to which the capture antigen is bound can be any suitable solid support or solid phase that facilitates separation of the capture antigen-anti-HCV antibody complex from the sample. Examples include a well of a plate, such as a microtiter plate, a test tube, a porous gel (e.g., silica gel, agarose, dextran, or gelatin), a polymeric film (e.g., polyacrylamide), beads (e.g., polystyrene beads or magnetic beads), a strip of a filter/membrane (e.g., nitrocellulose or nylon), microparticles (e.g., latex particles, magnetizable microparticles (e.g., microparticles having ferric oxide or chromium oxide cores and homo- or hetero-polymeric coats and radii of about 1-10 microns). The substrate can comprise a suitable porous material with a suitable surface affinity to bind antigens and sufficient porosity to allow access by detection antibodies. A microporous material is generally preferred, although a gelatinous material in a hydrated state can be used. Such porous substrates are preferably in the form of sheets having a thickness of about 0.01 to about 0.5 mm, preferably about 0.1 mm. While the pore size may vary quite a bit, preferably the pore size is from about 0.025 to about 15 microns, more preferably from about 0.15 to about 15 microns. The surface of such substrates can be activated by chemical processes that cause covalent linkage of an antibody to the substrate. Irreversible binding, generally by adsorption through hydrophobic forces, of the antigen to the substrate results; alternatively, a chemical coupling agent or other means can be used to bind covalently the antigen to the substrate, provided that such binding does not interfere with the ability of the antigen to bind to anti-HCV antibodies.

Alternatively, the antibody can be bound with microparticles, which have been previously coated with antigen. If desired, one or more capture reagents, such as a pair of polypeptides as described herein, each of which can be bound by an anti-HCV antibody, can be attached to solid phases in different physical or addressable locations (e.g., such as in a biochip configuration (see, e.g., U.S. Pat. No. 6,225,047, Int'l Pat. App. Pub. No. WO 99/51773; U.S. Pat. No. 6,329,209; Int'l Pat. App. Pub. No. WO 00/56934, and U.S. Pat. No. 5,242,828). If the capture reagent is attached to a mass spectrometry probe as the solid support, the amount of anti-HCV antibodies bound to the probe can be detected by laser desorption ionization mass spectrometry. Alternatively, a single column can be packed with different beads, which are derivatized with the one or more capture reagents, thereby capturing the anti-HCV antibody in a single place (see, antibody derivatized, bead-based technologies, e.g., the xMAP technology of Luminex (Austin, Tex.)).

After the test sample being assayed for anti-HCV antibodies is brought into contact with at least one capture antigen (for example, the first capture antigen), the mixture is incubated in order to allow for the formation of a first antigen (or multiple antigen)-anti-HCV antibody (or a fragment thereof) complex. The incubation can be carried out at a pH of from about 4.5 to about 10.0, at a temperature of from about 2° C. to about 45° C., and for a period from at least about one (1) minute to about eighteen (18) hours, preferably from about 1 to about 24 minutes, most preferably for about 4 to about 18 minutes. The immunoassay described herein can be conducted in one step (meaning the test sample, at least one capture antibody and at least one detection antibody are all added sequentially or simultaneously to a reaction vessel) or in more than one step, such as two steps, three steps, etc.

After formation of the (first or multiple) capture antigen/anti-HCV antibody complex, the complex is then contacted with at least one detection antibody (under conditions which allow for the formation of a (first or multiple) capture antigen/anti-HCV antibody/second antibody detection complex). The at least one detection antibody can be the second, third, fourth, etc. antibodies used in the immunoassay. If the capture antigen/anti-HCV antibody complex is contacted with more than one detection antibody, then a (first or multiple) capture antigen/anti-HCV antibody/(multiple) detection antibody complex is formed. As with the capture antigen (e.g., the first capture antigen), when the at least second (and subsequent) detection antibody is brought into contact with the capture antigen/anti-HCV antibody complex, a period of incubation under conditions similar to those described above is required for the formation of the (first or multiple) capture antigen/anti-HCV antibody/(second or multiple) detection antibody complex. Preferably, at least one detection antibody contains a detectable label. The detectable label can be bound to the at least one detection antibody (e.g., the second detection antibody) prior to, simultaneously with, or after the formation of the (first or multiple) capture antigen/anti-HCV antibody/(second or multiple) detection antibody complex. Any detectable label known in the art can be used (see discussion above, including Polak and Van Noorden (1997) and Haugland (1996)).

The detectable label can be bound to the antibodies either directly or through a coupling agent. An example of a coupling agent that can be used is EDAC (1-ethyl-3-(3-dimethylaminopropyl) carbodiimide, hydrochloride), which is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as CPSP-Acridinium Ester (i.e., 9-[N-tosyl-N-(3-carboxypropyl)]-10-(3-sulfopropyl)acridinium carboxamide) or SPSP-Acridinium Ester (i.e., N10-(3-sulfopropyl)-N-(3-sulfopropyl)-acridinium-9-carboxamide).

The (first or multiple) capture antigen/anti-HCV antibody/(second or multiple) detection antibody complex can be, but does not have to be, separated from the remainder of the test sample prior to quantification of the label. For example, if the at least one capture antigen (e.g., the first capture antigen) is bound to a solid support, such as a well or a bead, separation can be accomplished by removing the fluid (of the test sample) from contact with the solid support. Alternatively, if the at least first capture antigen is bound to a solid support, it can be simultaneously contacted with the anti-HCV antibody-containing sample and the at least one second detection antibody to form a first (multiple) antigen/anti-HCV antibody/second (multiple) antibody complex, followed by removal of the fluid (test sample) from contact with the solid support. If the at least one first capture antigen is not bound to a solid support, then the (first or multiple) capture antigen/anti-HCV antibody/(second or multiple) detection antibody complex does not have to be removed from the test sample for quantification of the amount of the label.

After formation of the labeled capture antigen/anti-HCV antibody/detection antibody complex (e.g., the first capture antigen/anti-HCV antibody/second detection antibody complex), the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified by detecting the light emitted either visually or by using luminometers, x-ray film, high speed photographic film, a CCD camera, etc. Once the amount of the label in the complex has been quantified, the concentration of anti-HCV antibody in the test sample is determined by use of a standard curve that has been generated using serial dilutions of anti-HCV antibody of known concentration. Other than using serial dilutions of anti-HCV antibodies, the standard curve can be generated gravimetrically, by mass spectroscopy and by other techniques known in the art.

In a chemiluminescent microparticle assay employing the ARCHITECT® analyzer, the conjugate diluent pH should be about 6.0+/−0.2, the microparticle coating buffer should be maintained at room temperature (i.e., at about 17 to about 27° C.), the microparticle coating buffer pH should be about 6.5+/−0.2, and the microparticle diluent pH should be about 7.8+/−0.2. Solids preferably are less than about 0.2%, such as less than about 0.15%, less than about 0.14%, less than about 0.13%, less than about 0.12%, or less than about 0.11%, such as about 0.10%.

FPIAs are based on competitive binding immunoassay principles. A fluorescently labeled compound, when excited by a linearly polarized light, will emit fluorescence having a degree of polarization inversely proportional to its rate of rotation. When a fluorescently labeled tracer-antibody complex is excited by a linearly polarized light, the emitted light remains highly polarized because the fluorophore is constrained from rotating between the time light is absorbed and the time light is emitted. When a "free" tracer compound (i.e., a compound that is not bound to an antibody) is excited by linearly polarized light, its rotation is much faster than the corresponding tracer-antibody conjugate produced in a competitive binding immunoassay. FPIAs are advantageous over RIAs inasmuch as there are no radioactive substances requiring special handling and disposal. In addition, FPIAs are homogeneous assays that can be easily and rapidly performed.

Commercially available anti-HCV antibodies as well as anti-IgG and anti-IgM antibodies can be used in the methods of assay and kits thereof. Commercially available antibodies include those available from Abnova (Walnut, Calif., and Taiwan) and GenWay Biotech, Inc. (San Diego, Calif.). See, also, European Pat. App. EP2099825 A2 regarding the preparation of anti-HCV antibodies.

Any suitable control composition can be used in the anti-HCV antibody immunoassays. The control composition generally comprises anti-HCV antibodies and any desirable additives.

Thus, in view of the above, a method of determining the presence, amount, or concentration of anti-HCV antibodies in a test sample is provided. The method comprises assaying the test sample for anti-HCV antibodies by an assay:
 (i) employing:
  (i') an immunodiagnostic reagent comprising at least one pair of first specific binding partners selected from the group consisting of:
  an isolated or purified polypeptide comprising the contiguous amino acids 1-198 of SEQ ID NO: 2 and an isolated or purified polypeptide comprising an epitope that is immunoreactive with an antibody that specifically binds to the NS3 region of HCV,
  an isolated or purified polypeptide comprising the contiguous amino acids 1-198 of SEQ ID NO: 2 and an isolated or purified polypeptide comprising the contiguous amino acids 1192-1457 of HCV,
  an isolated or purified polypeptide comprising the contiguous amino acids 1-198 of SEQ ID NO: 2 and an isolated or purified polypeptide comprising an epitope that is immunoreactive with an antibody that specifically binds to the NS3 region of HCV and an epitope that is immunoreactive with an antibody that specifically binds to the core region of HCV, and
  an isolated or purified polypeptide comprising the contiguous amino acids 1-198 of SEQ ID NO: 2 and an isolated or purified polypeptide comprising the contiguous amino acids 1192-1457 and 1-150 of HCV, and
  (ii') at least one detectable label, and
 (ii) comprising:
  comparing a signal generated by the detectable label as a direct or indirect indication of the presence, amount or concentration of anti-HCV antibodies in the test sample to a signal generated as a direct or indirect indication of the presence, amount or concentration of anti-HCV antibodies in a control or calibrator, which is optionally part of a series of calibrators in which each of the calibrators differs from the other calibrators in the series by the concentration of anti-HCV antibodies. The method can comprise the following steps:

(i) contacting the test sample with the immunodiagnostic reagent so as to form first specific binding partner/anti-HCV antibody complexes, (ii) contacting the first specific binding partner/anti-HCV antibody complexes with at least one detectably labeled second specific binding partner for anti-HCV antibody (e.g., anti-IgG antibody and anti-IgM antibody or polypeptides as described herein) so as to form first specific binding partner/anti-HCV antibody/second specific binding partner complexes, and (iii) determining the presence, amount or concentration of anti-HCV antibodies in the test sample by detecting or measuring the signal generated by the detectable label in the first specific binding partner/anti-HCV antibody/second specific binding partner complexes formed in (ii). Alternatively, the method can comprise the following steps:

(i) contacting the test sample with the immunodiagnostic reagent and simultaneously or sequentially, in either order, contacting the test sample with at least one detectably labeled second specific binding partner, which can compete with anti-HCV antibody for binding to the at least one pair of first specific binding partners and which comprises detectably labeled anti-HCV antibodies, wherein any anti-HCV antibody present in the test sample and the at least one detectably labeled second specific binding partner compete with each other to form first specific binding partner/anti-HCV antibody complexes and first specific binding partner/second specific binding partner complexes, respectively, and (ii) determining the presence, amount or concentration of anti-HCV antibodies in the test sample by detecting or measuring the signal generated by the detectable label in the first specific binding partner/second specific binding partner complex formed in (ii), wherein the signal generated by the detectable label in the first specific binding partner/second specific binding partner complex is inversely proportional to the amount or concentration of anti-HCV antibodies in the test sample. The polypeptides of which the immunodiagnostic reagent is comprised can be coated on microparticles. In this regard, the polypeptides of which the immunodiagnostic reagent is comprised can be co-coated on the same microparticles. When the polypeptides of which the immunodiagnostic reagent is comprised are co-coated on the same microparticles (e.g., a microparticle suspension containing 4% solids (4% weight/volume microparticles or 4 gr microparticles/100 mL microparticle suspension)), preferably the polypeptides are co-coated on the same microparticles in a ratio of about 1:2 to about 1:6, wherein, when the polypeptides are co-coated on the same microparticles in a ratio of about 1:2, the concentration of an isolated or purified polypeptide comprising the contiguous amino acids 1-198 of SEQ ID NO: 2 is at least about 40 µg/mL and the concentration of the other isolated or purified polypeptide is at least about 80 µg/mL. If the test sample was obtained from a patient, the method further comprise diagnosing, prognosticating, or assessing the efficacy of a therapeutic/prophylactic treatment of the patient. If the method further comprises assessing the efficacy of a therapeutic/prophylactic treatment of the patient, the method optionally can further comprise modifying the therapeutic/prophylactic treatment of the patient as needed to improve efficacy. The method can be adapted for use in an automated system or a semi-automated system.

Also, in view of the above, a method of determining the presence, amount, or concentration of anti-HCV antibodies in a test sample is provided. The method comprises assaying the test sample for anti-HCV antibodies by an assay:

(i) employing:

(i') an immunodiagnostic reagent comprising at least one pair of first specific binding partners selected from the group consisting of:

an isolated or purified polypeptide comprising a contiguous amino acid sequence that is at least about 95% identical to the contiguous amino acids 1-198 of SEQ ID NO: 2, wherein the isolated or purified polypeptide comprises (a) an epitope that is immunoreactive with an antibody that specifically binds to the core protein of HCV and (b) an epitope that is immunoreactive with an antibody that specifically binds to the NS4 region of HCV, and an isolated or purified polypeptide comprising an epitope that is immunoreactive with an antibody that specifically binds to the NS3 region of HCV, an isolated or purified polypeptide comprising a contiguous amino acid sequence that is at least about 95% identical to the contiguous amino acids 1-198 of SEQ ID NO: 2, wherein the isolated or purified polypeptide comprises (a) an epitope that is immunoreactive with an antibody that specifically binds to the core protein of HCV and (b) an epitope that is immunoreactive with an antibody that specifically binds to the NS4 region of HCV, and an isolated or purified polypeptide comprising the contiguous amino acids 1192-1457 of HCV, an isolated or purified polypeptide comprising a contiguous amino acid sequence that is at least about 95% identical to the contiguous amino acids 1-198 of SEQ ID NO: 2, wherein the isolated or purified polypeptide comprises (a) an epitope that is immunoreactive with an antibody that specifically binds to the core protein of HCV and (b) an epitope that is immunoreactive with an antibody that specifically binds to the NS4 region of HCV, and an isolated or purified polypeptide comprising an epitope that is immunoreactive with an antibody that specifically binds to the NS3 region of HCV and an epitope that is immunoreactive with an antibody that specifically binds to the core region of HCV, and an isolated or purified polypeptide comprising a contiguous amino acid sequence that is at least about 95% identical to the contiguous amino acids 1-198 of SEQ ID NO: 2, wherein the isolated or purified polypeptide comprises (a) an epitope that is immunoreactive with an antibody that specifically binds to the core protein of HCV and (b) an epitope that is immunoreactive with an antibody that specifically binds to the NS4 region of HCV, and an isolated or purified polypeptide comprising the contiguous amino acids 1192-1457 and 1-150 of HCV, and (ii') at least one detectable label, and (ii) comprising:

comparing a signal generated by the detectable label as a direct or indirect indication of the presence, amount or concentration of anti-HCV antibodies in the test sample to a signal generated as a direct or indirect indication of the presence, amount or concentration of anti-HCV antibodies in a control or calibrator, which is optionally part of a series of calibrators in which each of the calibrators differs from the other calibrators in the series by the concentration of anti-HCV antibodies. The method can comprise the following steps:

(i) contacting the test sample with the immunodiagnostic reagent so as to form first specific binding partner/anti-HCV antibody complexes, (ii) contacting the first specific binding partner/anti-HCV antibody complexes with at least one detectably labeled second specific binding partner for anti-HCV antibody (e.g., anti-IgG antibody and anti-IgM antibody or polypeptides as described herein) so as to form first specific binding partner/anti-HCV antibody/second specific binding partner complexes, and (iii) determining the presence, amount or concentration of anti-HCV antibodies in the test sample by detecting or measuring the signal generated by the detectable label in the first specific binding partner/anti-HCV antibody/second specific binding partner complexes formed in (ii). Alternatively, the method can comprise the following steps:

(i) contacting the test sample with the immunodiagnostic reagent and simultaneously or sequentially, in either order, contacting the test sample with at least one detectably labeled second specific binding partner, which can compete with anti-HCV antibody for binding to the at least one pair of first specific binding partners and which comprises detectably labeled anti-HCV antibodies, wherein any anti-HCV antibody present in the test sample and the at least one second specific binding partner compete with each other to form first specific binding partner/anti-HCV antibody complexes and a first specific binding partner/second specific binding partner complexes, respectively, and (ii) determining the presence, amount or concentration of anti-HCV antibodies in the test sample by detecting or measuring the signal generated by the detectable label in the first specific binding partner/second specific binding partner complex formed in (ii), wherein the signal generated by the detectable label in the first specific binding partner/second specific binding partner complex is inversely proportional to the amount or concentration of anti-HCV antibodies in the test sample. The polypeptides of which the immunodiagnostic reagent is comprised can be coated on microparticles. In this regard, the polypeptides of which the immunodiagnostic reagent is comprised can be co-coated on the same microparticles. When the polypeptides of which the immunodiagnostic reagent is comprised are co-coated on the same microparticles (e.g., a microparticle suspension containing 4% solids (4% weight/volume microparticles or 4 gr microparticles/100 mL microparticle suspension)), preferably the polypeptides are co-coated on the same microparticles in a ratio of about 1:2 to about 1:6, wherein, when the polypeptides are co-coated on the same microparticles in a ratio of about 1:2, the concentration of an isolated or purified polypeptide comprising the contiguous amino acids 1-198 of SEQ ID NO: 2 is at least about 40 µg/mL and the concentration of the other isolated or purified polypeptide is at least about 80 µg/mL. If the test sample was obtained from a patient, the method can further comprise diagnosing, prognosticating, or assessing the efficacy of a therapeutic/prophylactic treatment of the patient. If the method further comprises assessing the efficacy of a therapeutic/prophylactic treatment of the patient, the method optionally can further comprise modifying the therapeutic/prophylactic treatment of the patient as needed to improve efficacy. The method can be adapted for use in an automated system or a semi-automated system.

Generally, a predetermined level can be employed as a benchmark against which to assess results obtained upon assaying a test sample for anti-HCV antibodies. Generally, in making such a comparison, the predetermined level is obtained by running a particular assay a sufficient number of times and under appropriate conditions such that a linkage or association of analyte presence, amount or concentration with a particular stage or endpoint of a disease, disorder or condition (e.g., preeclampsia or cardiovascular disease) or with particular indicia can be made. Typically, the predetermined level is obtained with assays of reference subjects (or populations of subjects).

In particular, with respect to a predetermined level as employed for monitoring disease progression and/or treatment, the amount or concentration of anti-HCV antibodies may be "unchanged," "favorable" (or "favorably altered"), or "unfavorable" (or "unfavorably altered"). "Elevated" or "increased" refers to an amount or a concentration in a test sample that is higher than a typical or normal level or range (e.g., predetermined level), or is higher than another reference level or range (e.g., earlier or baseline sample). The term "lowered" or "reduced" refers to an amount or a concentration in a test sample that is lower than a typical or normal level or range (e.g., predetermined level), or is lower than another reference level or range (e.g., earlier or baseline sample). The term "altered" refers to an amount or a concentration in a sample that is altered (increased or decreased) over a typical or normal level or range (e.g., predetermined level), or over another reference level or range (e.g., earlier or baseline sample).

The typical or normal level or range for anti-HCV antibodies is defined in accordance with standard practice. Because the levels of anti-HCV antibodies in some instances will be very low, a so-called altered level or alteration can be considered to have occurred when there is any net change as compared to the typical or normal level or range, or reference level or range, that cannot be explained by experimental error or sample variation. Thus, the level measured in a particular sample will be compared with the level or range of levels determined in similar samples from a so-called normal subject. In this context, a "normal subject" is an individual with no detectable hepatitis, for example, and a "normal" (sometimes termed "control") patient or population is/are one(s) that exhibit(s) no detectable hepatitis, for example. Furthermore, given that anti-HCV antibodies are not routinely found at a high level in the majority of the human population, a "normal subject" can be considered an individual with no substantial detectable increased or elevated amount or concentration of anti-HCV antibodies, and a "normal" (sometimes termed "control") patient or population is/are one(s) that exhibit(s) no substantial detectable increased or elevated amount or concentration of anti-HCV antibodies. An "apparently normal subject" is one in which anti-HCV antibodies has not been or is being assessed. The level of an analyte is said to be "elevated" when the analyte is normally undetectable (e.g., the normal level is zero, or within a range of from about 25 to about 75 percentiles of normal populations), but is detected in a test sample, as well as when the analyte is present in the test sample at a higher than normal level. Thus, inter alia, the disclosure provides a method of screening for a subject having, or at risk of having, hepatitis, for example, as defined herein.

Accordingly, the methods described herein also can be used to determine whether or not a subject has or is at risk of developing hepatitis. Specifically, such a method can comprise the steps of:

(a) determining the concentration or amount in a test sample from a subject of anti-HCV antibodies (e.g., using the methods described herein, or methods known in the art); and (b) comparing the concentration or amount of anti-HCV antibodies determined in step (a) with a predetermined level, wherein, if the concentration or amount of anti-HCV antibodies determined in step (a) is favorable with respect to a predetermined level, then the subject is determined not to have or be at risk for hepatitis. However, if the concentration or amount of anti-HCV antibodies determined in step (a) is unfavorable with respect to the predetermined level, then the subject is determined to have or be at risk for hepatitis.

Additionally, provided herein is method of monitoring the progression of disease in a subject. Optimally the method comprising the steps of:

(a) determining the concentration or amount in a test sample from a subject of anti-HCV antibodies;

(b) determining the concentration or amount in a later test sample from the subject of anti-HCV antibodies; and (c) comparing the concentration or amount of anti-HCV antibodies as determined in step (b) with the concentration or amount of anti-HCV antibodies determined in step (a), wherein if the concentration or amount determined in step (b) is unchanged or is unfavorable when compared to the concentration or amount of anti-HCV antibodies determined in step (a), then the disease in the subject is determined to have continued, progressed or worsened. By comparison, if the concentration or amount of anti-HCV antibodies as determined in step (b) is favorable when compared to the concentration or amount of anti-HCV antibodies as determined in step (a), then the disease in the subject is determined to have discontinued, regressed or improved.

Optionally, the method further comprises comparing the concentration or amount of anti-HCV antibodies as determined in step (b), for example, with a predetermined level. Further, optionally the method comprises treating the subject with one or more pharmaceutical compositions for a period of time if the comparison shows that the concentration or amount of anti-HCV antibodies as determined in step (b), for example, is unfavorably altered with respect to the predetermined level.

Still further, the methods can be used to monitor treatment in a subject receiving treatment with one or more pharmaceutical compositions. Specifically, such methods involve providing a first test sample from a subject before the subject has been administered one or more pharmaceutical compositions. Next, the concentration or amount in a first test sample from a subject of anti-HCV antibodies is determined (e.g., using the methods described herein or as known in the art). After the concentration or amount of anti-HCV antibodies is determined, optionally the concentration or amount of anti-HCV antibodies is then compared with a predetermined level. If the concentration or amount of anti-HCV antibodies as determined in the first test sample is lower than the predetermined level, then the subject is not treated with one or more pharmaceutical compositions. However, if the concentration or amount of anti-HCV antibodies as determined in the first test sample is higher than the predetermined level, then the subject is treated with one or more pharmaceutical compositions for a period of time. The period of time that the subject is treated with the one or more pharmaceutical compositions can be determined by one skilled in the art (for example, the period of time can be from about seven (7) days to about two years, preferably from about fourteen (14) days to about one (1) year).

During the course of treatment with the one or more pharmaceutical compositions, second and subsequent test samples are then obtained from the subject. The number of test samples and the time in which said test samples are obtained from the subject are not critical. For example, a second test sample could be obtained seven (7) days after the subject is first administered the one or more pharmaceutical compositions, a third test sample could be obtained two (2) weeks after the subject is first administered the one or more pharmaceutical compositions, a fourth test sample could be obtained three (3) weeks after the subject is first administered the one or more pharmaceutical compositions, a fifth test sample could be obtained four (4) weeks after the subject is first administered the one or more pharmaceutical compositions, etc.

After each second or subsequent test sample is obtained from the subject, the concentration or amount of anti-HCV antibodies is determined in the second or subsequent test sample is determined (e.g., using the methods described herein or as known in the art). The concentration or amount of anti-HCV antibodies as determined in each of the second and subsequent test samples is then compared with the concentration or amount of anti-HCV antibodies as determined in the first test sample (e.g., the test sample that was originally optionally compared to the predetermined level). If the concentration or amount of anti-HCV antibodies as determined in step (c) is favorable when compared to the concentration or amount of anti-HCV antibodies as determined in step (a), then the disease in the subject is determined to have discontinued, regressed or improved, and the subject should continue to be administered the one or pharmaceutical compositions of step (b). However, if the concentration or amount determined in step (c) is unchanged or is unfavorable when compared to the concentration or amount of anti-HCV antibodies as determined in step (a), then the disease in the subject is determined to have continued, progressed or worsened, and the subject should be treated with a higher concentration of the one or more pharmaceutical compositions administered to the subject in step (b) or the subject should be treated with one or more pharmaceutical compositions that are different from the one or more pharmaceutical compositions administered to the subject in step (b). Specifically, the subject can be treated with one or more pharmaceutical compositions that are different from the one or more pharmaceutical compositions that the subject had previously received to decrease or lower said subject's anti-HCV antibodies level.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years after the first test sample from the subject is obtained. When used to monitor disease progression, the above assay can be used to monitor the progression of disease in subjects suffering from acute conditions. Acute conditions, also known as critical care conditions, refer to acute, life-threatening diseases or other critical medical conditions involving, for example, the cardiovascular system or excretory system. Typically, critical care conditions refer to those conditions requiring acute medical intervention in a hospital-based setting (including, but not limited to, the emergency room, intensive care unit, trauma center, or other emergent care setting) or administration by a paramedic or other field-based medical personnel. For critical care conditions, repeat monitoring is generally done within a shorter time frame, namely, minutes, hours or days (e.g., about 1 minute, about 5 minutes, about 10 minutes, about 15 minutes, about 30 minutes, about 45 minutes, about 60 minutes, about 2 hours, about 3 hours, about 4 hours, 4 about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days or about 7 days), and the initial assay likewise is generally done within a shorter timeframe, e.g., about minutes, hours or days of the onset of the disease or condition.

The assays also can be used to monitor the progression of disease in subjects suffering from chronic or non-acute conditions. Non-critical care or, non-acute conditions, refers to conditions other than acute, life-threatening disease or other critical medical conditions involving, for example, the cardiovascular system and/or excretory system. Typically, non-acute conditions include those of longer-term or chronic duration. For non-acute conditions, repeat monitoring generally is done with a longer timeframe, e.g., hours, days, weeks, months or years (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5. years, about 6.0 years, about 6.5 years, about 7.0 years, about 7.5 years, about 8.0 years, about 8.5 years, about 9.0 years, about 9.5 years or about 10.0 years), and the initial assay likewise generally is done within a longer time frame, e.g., about hours, days, months or years of the onset of the disease or condition.

Furthermore, the above assays can be performed using a first test sample obtained from a subject where the first test sample is obtained from one source, such as urine, serum or plasma. Optionally the above assays can then be repeated using a second test sample obtained from the subject where the second test sample is obtained from another source. For example, if the first test sample was obtained from urine, the second test sample can be obtained from serum or plasma. The results obtained from the assays using the first test sample and the second test sample can be compared. The comparison can be used to assess the status of a disease or condition in the subject.

Moreover, the present disclosure also relates to methods of determining whether a subject predisposed to or suffering from hepatitis will benefit from treatment. In particular, the disclosure relates to HCV companion diagnostic methods and products. Thus, the method of "monitoring the treatment of disease in a subject" as described herein further optimally also can encompass selecting or identifying candidates for therapy.

Thus, in particular embodiments, the disclosure also provides a method of determining whether a subject having, or at risk for, hepatitis is a candidate for therapy. Generally, the subject is one who has experienced some symptom of hepatitis or who has actually been diagnosed as having, or being at risk for, hepatitis and/or who demonstrates an unfavorable concentration or amount of anti-HCV antibodies or a fragment thereof, as described herein.

The method optionally comprises an assay as described herein, where analyte is assessed before and following treatment of a subject with one or more pharmaceutical compositions (e.g., particularly with a pharmaceutical related to a mechanism of action involving HCV), with immunosuppressive therapy, or by immunoabsorption therapy, with anti-angiogenic therapy, or where analyte is assessed following such treatment and the concentration or the amount of analyte is compared against a predetermined level. An unfavorable concentration or amount of analyte observed following treatment confirms that the subject will not benefit from receiving further or continued treatment, whereas a favorable concentration or amount of analyte observed following treatment confirms that the subject will benefit from receiving further or continued treatment. This confirmation assists with management of clinical studies, and provision of improved patient care.

Adaptation of Kit and Method

The kit (or components thereof), as well as the method of determining the concentration of anti-HCV antibodies in a test sample by an immunoassay as described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., antigen) is attached (which can impact sandwich formation and analyte reactivity), and the length and timing of the capture, detection and/or any optional wash steps. Whereas a non-automated format such as an ELISA may require a relatively longer incubation time with sample and capture reagent (e.g., about 2 hours), an automated or semi-automated format (e.g., ARCHITECT®, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT®) may have a relatively shorter incubation time (e.g., approximately 4 minutes for the ARCHITECT®).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the detection antibody labeled with alkaline phosphatase (or other label). Within the fluid pouch of the cartridge is an aqueous reagent that includes p-aminophenol phosphate.

In operation, a sample suspected of containing anti-HCV antibody is added to the holding chamber of the test cartridge and the cartridge is inserted into the I-STAT® reader. After the detection antibody has dissolved into the sample, a pump element within the cartridge forces the sample into a conduit containing the chip. Here it is oscillated to promote formation of the sandwich between the capture antigen, anti-HCV antibody, and the labeled detection antibody. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of anti-HCV antibody in the sample by means of an embedded algorithm and factory-determined calibration curve.

It further goes without saying that the methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Patent Application No. 61/142,048 filed Dec. 31, 2008, and U.S. patent application Ser. No. 12/650,241, improved signal generation may be obtained, e.g., in an I-STAT® cartridge format, using a nucleic acid sequence linked to the signal antibody as a signal amplifier.

Composition for Inducing Immune Response to HCV

A composition comprising (i) an immune response-inducing amount of a polypeptide comprising the contiguous amino acids 1-198 of SEQ ID NO: 2 or (ii) a vector that expresses an immune response-inducing amount of the aforementioned polypeptide is also provided. In addition, a composition comprising (i) an immune response-inducing amount of a polypeptide comprising a contiguous amino acid sequence that is at least about 95% (such as at least about 96%, at least about 97%, at least about 98%, or at least about 99%) identical to the contiguous amino acids 1-198 of SEQ ID NO: 2, wherein the isolated or purified polypeptide comprises an epitope that is immunoreactive with an antibody that specifically binds to the core protein of HCV and an epitope that is immunoreactive with an antibody that specifically binds to the NS4 region of HCV, or (ii) a vector that expresses an immune response-inducing amount of the aforementioned polypeptide is also provided. The aforementioned compositions can further comprise an adjuvant, such as aluminum hydroxide, aluminum phosphate, or aluminum oxide, or a composition that consists of a mineral oil, such as Marcol 52, or a vegetable oil and one or more emulsifying agents. If desired, the aforementioned compositions can comprise one or more additional immunogens, such as polypeptides (or vectors expressing such polypeptides) from hepatitis A virus or hepatitis B virus. Various compositions for inducing an immune response, suitable for different routes of administration, and methods of preparing such compositions are known in the art and are described, for example, in "Remington: The Science and Practice of Pharmacy" (formerly "Remington's Pharmaceutical Sciences"); Gennaro, A., Lippincott, Williams & Wilkins, Philadelphia, Pa. (2000). Typically, such compositions are prepared as injectables, either as liquid solutions or suspensions, and administered parenterally, by injection, for example, either subcutaneously or intramuscularly.

Method of Inducing Immune Response to HCV

In view of the foregoing, a method of inducing an immune response to HCV is also provided. The method comprises administering to an individual a composition comprising an immune response-inducing amount of a polypeptide comprising the contiguous amino acids 1-198 of SEQ ID NO: 2 and/or a polypeptide comprising a contiguous amino acid sequence that is at least about 95% (such as at least about 96%, at least about 97%, at least about 98%, or at least about 99%) identical to the contiguous amino acids 1-198 of SEQ ID NO: 2, wherein the latter polypeptide comprises (i) an epitope that is immunoreactive with an antibody that specifically binds to the core protein of HCV and (ii) an epitope that is immunoreactive with an antibody that specifically binds to the NS4 region of HCV. Alternatively, the method comprises administering to an individual a live vector, such as a bacterial cell vector, which infects an individual, is stably transformed, and expresses an immune response-inducing amount of a polypeptide comprising the contiguous amino acids 1-198 of SEQ ID NO: 2 and/or a polypeptide comprising a contiguous amino acid sequence that is at least about 95% (such as at least about 96%, at least about 97%, at least about 98%, or at least about 99%) identical to the contiguous amino acids 1-198 of SEQ ID NO: 2, wherein the latter polypeptide comprises (i) an epitope that is immunoreactive with an antibody that specifically binds to the core protein of HCV and (ii) an epitope that is immunoreactive with an antibody that specifically binds to the NS4 region of HCV. The composition is administered in an amount sufficient to induce an immune response, and desirably protection upon challenge. Generally, about 2 μg to about 250 μg of antigen are administered in a single dose. Such compositions can contain one or more other immunogens, such as polypeptides (or vectors expressing such polypeptides) from hepatitis A virus or hepatitis B virus. Such a cocktail vaccine has the advantage that an immune response against several pathogens can be induced with a single administration. The individual can be inoculated with the composition in any way known to artisans skilled in this field. For example, the composition can be delivered by injection or in a form of an oral vaccine. Booster shots are optional, if necessary. Preferably, the inoculation is performed before infection. Newly born animals, even an embryo, may also be inoculated with the composition to produce better immunity.

EXAMPLES

The following examples serve to illustrate the present disclosure. The examples are not intended to limit the scope of the claimed invention in any way.

Example 1

This example describes the design and construction of a plasmid encoding HCV-1 core amino acids 8-125 and HCV-1 NS4 amino acids 1688-1740 and 1915-1940.

A nucleotide sequence encoding the HCV-1 core amino acids 8-125, the HCV-1 NS4 amino acids 1688-1740 and 1915-1940, and a carboxyl-terminal hexa-histidine tag sequence (6×His) (SEQ ID NO: 5), which facilitates purification of the expressed protein, was constructed by synthetic nucleotide synthesis (GenScript Corp.; Piscataway, N.J.) utilizing codons commonly found in *E. coli* to optimize expression in *E. coli*. The nucleotide construct was designated 9NB44H and was inserted into the plasmid pUC57 (GenScript Corp.) as an Eco RI/Bam HI restricted fragment. The resulting recombinant plasmid was designated pUC57-9NB44H.

Example 2

This example describes the cloning of a recombinant plasmid encoding HCV-1 core amino acids 8-125 and HCV-1 NS4 amino acids 1688-1740 and 1915-1940.

The recombinant plasmid pUC57-9NB44H of Example 1 was digested with Eco RI and Bam HI to liberate the 628 base pair (bp) insert encoding the HCV-1 core amino acids 8-125 and HCV-1 NS4 amino acids 1688-1740 and 1915-1940. The 628-bp fragment was isolated and ligated into the bacterial expression vector pKRR826 ("pL"; Abbott Laboratories, Abbott Park, Ill., proprietary vector) digested with Eco RI and Bam HI using the LigaFast Rapid DNA Ligation System (Promega, Madison, Wis.). The bacterial expression vector pKRR826 uses the pL transcriptional promoter of bacteriophage lambda (see, e.g., European Patent No. EP1004023B1 and U.S. Pat. No. 5,859,193 A) under the control of a temperature-sensitive cI repressor (Bernard et al., Gene 5: 59 (1979)). The resulting recombinant vector was designated pL-9NB44H and transformed into XL1-Blue competent cells (Stratagene, La Jolla, Calif.). A clone of transformed XL1-Blue cells containing the appropriately sized insert was identified via restriction enzyme digestion of purified plasmid DNA.

Example 3

This example describes the recombinant expression and purification of a protein containing HCV-1 core amino acids 8-125 and HCV-1 NS4 amino acids 1688-1740 and 1915-1940.

The recombinant vector pL-9NB44H plasmid was isolated from the clone of transformed XL1-Blue cells of Example 2 and transformed into *E. coli* BL21 cells (Stratagene, La Jolla, Calif.) and *E. coli* HS36 cells (Abbott Laboratories, proprietary cell line). Sequencing was conducted to confirm that the desired regions of the HCV core and HCV NS4 were encoded.

*E. coli* BL21 cells transformed with pL-9NB44H were streaked onto an LB-Amp agar plate and grown overnight at 37° C. The next day a single, well-isolated colony was picked from the plate using a sterile probe, and the cells were transferred into 5 mL of LB or TB medium containing 50 mg/mL ampicillin. Cells were grown overnight at 37° C. The next day the 5 mL culture was transferred to 100 mL of TB or LB medium containing 50 mg/mL ampicillin. The culture was grown at 30° C. in a shaking water bath until the optical density at 600 nm reached approximately 0.60. The culture was then transferred to a 42° C. water bath to induce protein expression and incubated at 42° C. for 3 hours. Cells were then collected by centrifugation, and the medium was discarded.

Cells were suspended in 10 mL lysis buffer (40 mM Tris, pH 8.0, 0.5% Triton-X100, 1 mM EDTA, 1 M NaCl, and 10 mM $MgCl_2$) per gram of cells. Cells were lysed by the addition of 229 units Benzonase (Novagen, Madison, Wis.) per gram of cells and 42 mg lysozyme per gram of cells and by vigorous mixing for two minutes using a hand-held homogenizer. Phenylmethylsulfonyl fluoride was added to the mixture (0.75 mL of 10 mg/mL solution), which was then homogenized for another two minutes. The mixture was incubated in a shaking water bath at 37° C. for 60 minutes. The lysate was then centrifuged (16,800×g, 35 minutes), and the supernatant was discarded. The pelleted material was resuspended by the addition of 10 mL urea-containing solubilization buffer (40 mM Tris, pH 8.0, 0.5% Triton-X100, 1 mM EDTA, 1M NaCl, 6 M urea, and 10 mM $MgCl_2$) per gram of the original cell pellet using a hand-held homogenizer for two minutes. The mixture was then incubated at 37° C. in a shaking water bath for 60 minutes. The solubilized pellet was then centrifuged (16,800×g, 35 minutes), and the pellet was discarded. The supernatant was filtered through a 0.8 μm low protein binding filter followed immediately by a second filtration through a 0.2 μm low protein binding filter.

Affinity chromatography was performed by adding 2.5 mL of Nickel-Sepharose resin slurry (GE Life Sciences, Piscataway, N.J., catalog no. 17-5268-02) directly to the solubilized protein solution (i.e., approximately 0.70 grams slurry per gram starting cell pellet weight). The resin-protein solution was incubated at room temperature for approximately 60 minutes with rotating mixing. The resin was then separated from the liquid by centrifugation (1660×g, 7 minutes). The liquid supernatant was removed and saved. The resin containing the protein-of-interest was washed twice with 35 mL of 20 mM Tris, pH 8.4, 1.0 M NaCl, 3.0 M urea, 18 mM imidazole, and 0.01% Triton-X100 by gentle inversion (10 times) followed by centrifugation as above. The resin was then washed twice with buffer containing 20 mM Tris, pH 8.4, 1.5 M NaCl, 3.0 M urea, 18 mM imidazole, and 0.01% Triton-X100 by gentle inversion (10 times) followed by centrifugation as above. The resin was then washed once more with 10 mL of this same buffer. The wash buffer was discarded while the resin containing the bound protein was saved.

Protein bound to the Nickel-Sepharose resin was eluted by using 6.0 mL of buffer containing 15 mM sodium phosphate, pH 7.4, 30 mM NaCl, 3.0 M urea, and 100 mM EDTA. The resuspended resin was mixed end-over-end at room temperature for approximately 30 minutes. The resin was separated from the liquid by centrifugation (1660×g, 7 minutes), and the supernatant containing the eluted protein was saved. A second elution step was then performed as described above, and the supernatant was saved. The eluate (2.5 mL aliquot) was dialyzed for approximately 1 hour at room temperature using a 10,000 Da cutoff membrane filter cassette (Pierce, Inc., Rockford, Ill.) against 500 mL of buffer containing 50 mM sodium phosphate, pH 7.4, 100 mM NaCl, and 3.0 M urea. Dialysis then continued overnight at 4° C. against 1,000 mL of fresh buffer. Two more dialysis steps were performed against 1,000 mL each of fresh buffer at 4° C. for 2-3 hours. The protein solution was then removed from the dialysis cassette, and the protein concentration was determined by measurement of the UV absorbance: [(OD 280 nm-OD 320 nm)/1.8636]× dilution factor=protein concentration in mg/mL; where OD=optical density or absorbance and the absorbance of a 1 mg/mL solution=1.8636 as calculated from the amino acid sequence (Pace et al., Protein Science 4: 2411-2423 (1995)).

SDS-PAGE analysis of affinity purified 9NB44H revealed full-length proteins and fragments. The amount of fragments observed was significantly lower in *E. coli* HS36 cells as compared to *E. coli* BL21 cells.

Example 4

This example describes the preparation of paramagnetic particles co-coated with 9NB44H and HC43H recombinant antigen.

Paramagnetic microparticles co-coated with HC43H and 9NB44H recombinant proteins were prepared. An 8 mL aliquot of microparticles (5% weight/volume, Spherotech, Inc, Lake Forest, Ill.) was separated from solution using a magnetic stand (Promega, Madison, Wis.), and the solution was removed. The particles were then resuspended in 10.0 mL of a coating buffer (2-(N-Morpholino) ethanesulfonic acid (MES) buffer, pH 6.0) and separated from the solution using a magnetic field. This was repeated once more.

The washed microparticles were activated by re-suspension in 5.0 ml of MES buffer and the addition of 0.1 mL of 100 mg/mL N-Ethyl-N'-(3-dimethylaminopropyl)carbodiimide hydrochloride. The microparticle solution was mixed end-over-end for 10 minutes at room temperature. A recombinant antigen mixture (902 μL of HC43H (1.109 mg/ml; amino acids 1192-1457 (33c) and 1-150 (core) of the HCV sequence and a 6×His tag (SEQ ID NO: 5) at the carboxyl terminus; available from Abbott Laboratories, Abbott Park, Ill.), 150 μl of 9NB44H (2.06 mg/ml), and 125 μl of DTT (dithiothritol; 400 mg/ml) were added to 3,823 μL of MES) were added to the activated microparticles. The resulting microparticle/protein solution was mixed end-over-end for one hour at room temperature. The microparticles were then resuspended in 10 mL of the diluent (MES, NaCl, EDTA, and DTT), and separated from the solution using a magnetic field. This was repeated once more. The microparticles were diluted to 1% concentration by re-suspension in 40 mL of the diluent (MES, NaCl, EDTA, and DTT).

Example 5

This example describes the comparison of an automated anti-HCV antibody immunoassay employing paramagnetic microparticles co-coated with 9NB44H and HC43H recombinant antigen in accordance with the present disclosure and an automated anti-HCV antibody immunoassay employing commercially available microparticles co-coated with C100-3 and HC43.

The microparticles prepared as described in Example 4 were tested for their ability to detect anti-HCV antibodies using an automated immunoanalyzer that utilizes paramagnetic microparticles and chemiluminescent conjugates (AR-CHITECT® system; Abbott Laboratories, Abbott Park, Ill.; see Quinn, "Bulk Reagent Random-Access Analyzer: ARCHITECT i2000," pages 363-367, In: The Immunoassay Handbook, $2^{nd}$ ed., Ward, ed., Nature Publishing Group, London, UK; and U.S. Pat. Nos. 5,795,784 and 5,856,194). The performance of the microparticles was compared with microparticles from a commercially available anti-HCV antibody immunoassay (06C37) for use with the ARCHI-TECT® system (Abbott Laboratories, Abbott Park, Ill.).

The commercially available anti-HCV antibody immunoassay employs microparticles coated with the HC43 antigen and microparticles coated with the C100-3 antigen. The HC43 antigen is expressed in *E. coli* and is composed of two noncontiguous coding regions of the HCV genome sequence, i.e., the first region contains amino acids 1192 to 1457 (33c) of the HCV sequence (NS3 coding region) and the second region contains amino acids 1 to 150 of the HCV sequence (HCV core coding region) (available from Chiron, Emeryville, Calif.). The C100-3 antigen is expressed in *Saccharomyces cerevisiae* (yeast) and is a chimeric fusion protein composed of 154 amino acids of human superoxide dismutase (hSOD), five linked amino acids, amino acids 1569 to 1931 of the HCV polyprotein (putative nonstructural (NS4) coding region), and five additional amino acids at the carboxyl terminus (available from Chiron, Emeryville, Calif.; see also U.S. Pat. No. 5,350,671).

As noted above in Example 4, the microparticles prepared in accordance with the present disclosure are co-coated with the HC43H antigen and the 9NB44H antigen. The HC43H protein is expressed in *E. coli* and is composed of two noncontiguous coding regions of the HCV genome sequence, i.e., the first region contains amino acids 1192 to 1457 (33c) of the HCV sequence (NS3 coding region) and the second region contains amino acids 1 to 150 of the HCV sequence (HCV core coding region), and a 6×His tag (SEQ ID NO: 5) at the carboxyl terminus. The 9NB44H is expressed in *E. coli* and is composed of two noncontiguous coding regions of the HCV genome sequence, i.e., the first region contains amino acids 8 to 125 of the HCV sequence (HCV core coding region) and the second region contains amino acids 1688-1740 and 1915-1940 of the putative nonstructural (NS4) region of HCV, and a 6×His tag (SEQ ID NO: 5) at the carboxyl terminus The microparticles prepared in accordance with the present disclosure and the microparticles used in the commercially available immunoassay were compared using a two-step antibody assay format. In the two-step antibody assay format, 10 µl of sample, 50 µl of specimen diluent, and 50 µl of coated paramagnetic microparticles were mixed in a reaction vessel, vortexed, and incubated for 18 minutes. Following this incubation, the microparticles were sequestered at the side of the reaction vessel using a magnet while the reaction supernatant was removed. The microparticles were subsequently washed with water/detergent solution. Antibodies present in the samples and captured on the microparticles were retained during the washing step(s) Immediately following washing, conjugates containing acridinium-labeled anti-human IgG and acridinium labeled anti-human IgM (see, for example, U.S. Pat. No. 6,727,092 B2) in conjugate diluent buffer (50 mM MES at pH 6.6 with 1.4% volume/volume Triton-X405, 0.4 M NaCl, and 1% weight/volume bovine serum albumin) were added to the reaction vessel, which was vortexed and then allowed to incubate for 4 minutes. Incubation was followed by a second wash step, activation of the acridinium, and simultaneous measurement of light output, which is proportional to the amount of conjugate bound onto the microparticles. The amount of light emitted is proportional to the amount of antibody in the sample and is expressed in relative light units (RLU). The presence or absence of antibody in the test sample is determined by comparing the RLU obtained from the test sample to that obtained for the cutoff value (obtained by multiplying the RLU's in the calibrator sample by 0.074). Samples with RLU's above the cutoff value were considered reactive. (The calibrator is prepared by diluting a sample known to be positive for antibodies to HCV in human plasma that is negative for antibodies to HCV. The cutoff is determined by selecting an RLU range or value that best separates samples known to be negative for antibodies to HCV from samples known to be positive for antibodies to HCV).

A specificity study was performed by testing specimens from random U.S. blood donors, who are typically at "low risk" for HCV infection. One would expect that less than 0.5% of these specimens would be reactive in an anti-HCV test.

The microparticles prepared in accordance with the present disclosure and the microparticles used in the commercially available immunoassay were compared in a specificity study by testing 4,603 samples from random U.S. donors, 1,909 samples from German blood donors (tested in Delkenheim, Germany), and 1,845 German blood donors (tested in Giessen, Germany). The number of true negative samples was determined for both assays and expressed as specificity. A 100% specificity value would indicate that there are no false positive samples. As shown in Table 1, the two assays had comparable specificity, each at 99.89%. These data indicated that the microparticles prepared in accordance with the present disclosure were equivalent to the microparticles used in the commercially available immunoassay.

TABLE 1

| Site (n = number of samples) | Anti-HCV Test with Microparticles used in Commercially Available Immunoassay % specificity (true negatives divided by total true negatives) | Anti-HCV Test with Microparticles prepared in accordance with present disclosure % specificity (true negatives divided by total true negatives) |
| --- | --- | --- |
| Lake County (n = 4,603) | 99.85% | 99.85% |
| Delkenheim (n = 1,909) | 99.89% | 99.89% |
| Giessen (n = 1,845) | 100% | 100% |

The microparticles prepared in accordance with the present disclosure and the microparticles used in the commercially available immunoassay were also compared for their ability to detect anti-HCV antibodies from bleeds selected from 39 seroconversion panels. Seroconversion panels are typically a series of samples taken from an individual whose antibody status for anti-HCV changes from negative to positive Immunoassays designed to detect antibodies are often evaluated on these seroconversion panels to determine assays that provide the earliest possible detection of antibodies in these series of samples.

A total of 21 seroconversion panels were obtained from Zeptometrix (Buffalo, N.Y.). A total of 198 samples were obtained from 21 individuals. Fifty five samples were reactive with the microparticles used in the commercially available immunoassay, while 56 samples were reactive with the microparticles prepared in accordance with the present disclosure. One serum sample from panel BCP 6214 was detected earlier with the microparticles used in the commercially available immunoassay, while one serum sample from panel BCP6223 and one serum sample from BCP10041 were detected earlier with the microparticles prepared in accordance with the present disclosure.

Eighteen seroconversion panels were obtained from BBI SeraCare Life Sciences (Milford, Mass.). Seventy nine samples were reactive with the microparticles used in the commercially available immunoassay, while 80 samples were reactive with the microparticles prepared in accordance with the present disclosure. One serum sample from PHV909 was reactive with the microparticles prepared in accordance with the present disclosure but non-reactive with the microparticles used in the commercially available immunoassay.

Thus, overall, 331 samples were tested. As shown in Table 2, while the microparticles used in the commercially available immunoassay detected 134 samples, the microparticles prepared in accordance with the present disclosure detected 136 samples. Thus, use of the microparticles prepared in accordance with the present disclosure on the ARCHITECT® system (Abbott Laboratories, Abbott Park, Ill.) was more sensitive than use of the microparticles from the commercially available immunoassay.

TABLE 2

| Panel | No. of bleeds | Number of reactive bleeds | |
|---|---|---|---|
| | | Commercially Available Microparticles | Present Disclosure Microparticles |
| BCP6212 | 9 | 6 | 6 |
| BCP6213 | 12 | 2 | 2 |
| BCP6214 | 13 | 6 | 5 |
| BCP6215 | 4 | 1 | 1 |
| BCP6216 | 7 | 1 | 1 |
| BCP6222 | 8 | 1 | 1 |
| BCP6223 | 22 | 3 | 4 |
| BCP6224 | 6 | 1 | 1 |
| BCP6225 | 19 | 1 | 1 |
| BCP6226 | 12 | 4 | 4 |
| BCP6227 | 7 | 2 | 2 |
| BCP6228 | 12 | 3 | 3 |
| BCP6229 | 8 | 4 | 4 |
| BCP9041 | 8 | 4 | 4 |
| BCP9044 | 6 | 2 | 2 |
| BCP9045 | 8 | 2 | 2 |
| BCP9047 | 10 | 4 | 4 |
| BCP9054 | 10 | 1 | 1 |
| BCP9058 | 5 | 2 | 2 |
| BCP10041 | 3 | 1 | 2 |
| BCP10165 | 9 | 4 | 4 |
| Subtotal 21 Panels | 198 | 55 | 56 |
| PHV901 | 11 | 9 | 9 |
| PHV904 | 7 | 4 | 4 |
| PHV905 | 9 | 6 | 6 |
| PHV906 | 7 | 7 | 7 |
| PHV907 | 7 | 3 | 3 |
| PHV908 | 13 | 8 | 8 |
| PHV909 | 3 | 1 | 2 |
| PHV910 | 5 | 3 | 3 |
| PHV911 | 5 | 3 | 3 |
| PHV912 | 3 | 1 | 1 |
| PHV913 | 4 | 2 | 2 |
| PHV914 | 9 | 5 | 5 |
| PHV915 | 4 | 2 | 2 |
| PHV917 | 10 | 6 | 6 |
| PHV918 | 8 | 2 | 2 |
| PHV919 | 7 | 3 | 3 |
| PHV920 | 10 | 7 | 7 |
| PHV911 | 11 | 7 | 7 |
| Subtotal (18 panels) | 133 | 79 | 80 |
| Total (39 panels) | 331 | 134 | 136 |

Example 6

This example describes the comparison of an automated anti-HCV antibody immunoassay employing paramagnetic microparticles co-coated with different ratios of 9NB44H and HC43H recombinant antigen in accordance with the present disclosure.

Raw paramagnetic particles were coated at different ratios of 9NB44H and HC43H as shown in Table 3. Negative control (pooled plasma samples that tested negative for antibodies to HCV), positive control (anti-HCV positive sample diluted in negative control), calibrator (highly reactive anti-HCV positive sample), panel A (sample reactive only for antibodies to the HCV core protein), panel B (sample reactive only for antibodies to the NS3 protein), and anti-NS4 (sample reactive only for antibodies to the NS4 protein; actually, this sample is a chimeric antibody consisting of a specific anti-NS4 binding site at the amino end of the molecule (murine-based antibody) and the human IgG antibody) were evaluated by the signal generated (RLUs) and by the relative strength of the signal based on a cutoff (the cutoff value, which separates negative results from positive results, may be calculated as 0.074 times the calibrator RLUs). In general, the calibrator values are between about 377,000 RLUs and 417,000 RLUs, and the cutoff is usually between about 28,000 RLUs and 31,000 RLUs. For this analysis a cutoff value that was 0.074 times the calibrator RLUs was selected. The positive control value is utilized to determine that a given run is successful. For a given run to be successful the S/CO value should be between 2.0 and 5.0. For samples that may represent patient samples (e.g., Panel A and Panel B), higher S/CO values are desired. As noted in Table 3, for Panel A, all coating conditions for the microparticles of the present disclosure, except one (HC43H Ag at 40 μg/mL and 9NB44H Ag at 20 μg/mL), showed equal or better S/CO values when compared to the commercially available microparticles. For Panel B, 4 of the 6 conditions showed higher S/CO's when compared to the commercially available microparticles. Thus, microparticles co-coated with various ratios of HC43H and 9NB44H in accordance with the present disclosure perform better than the commercially available microparticles.

TABLE 3

| | Present Disclosure Microparticles Co-Coated at 4% Solids⁺ | | | | | | |
|---|---|---|---|---|---|---|---|
| | HC43H Ag | | | | | | |
| | 40 μg/ml | 80 μg/ml | 120 μg/ml | 40 μg/ml | 80 μg/ml | 120 μg/ml | |
| | 9NB44H Ag | | | | | | Commercially |
| | 40 μg/ml | 40 μg/ml | 40 μg/ml | 20 μg/ml | 20 μg/ml | 20 μg/ml | Available Microparticles |
| Negative Control | 835* (0.03) | 1,331 (0.04) | 1,399 (0.05) | 811 (0.03) | 1,018 (0.03) | 1,477 (0.05) | 1,444 (0.06) |
| Positive Control | 84,816 (2.97) | 100,236 (3.33) | 95,577 (3.31) | 79,057 (2.83) | 94,161 (3.23) | 92,229 (2.98) | 75,083 (2.91) |
| Calibrator | 386,592 (13.51) | 406,685 (13.51) | 390,523 (13.51) | 377,558 (13.51) | 393,747 (13.51) | 417,913 (13.51) | 348,556 (13.51) |
| Panel A (anti-core) | 113,636 (3.97) | 139,965 (4.65) | 119,523 (4.14) | 106,090 (3.79) | 125,526 (4.31) | 125,179 (4.05) | 102,306 (3.97) |

TABLE 3-continued

| | Present Disclosure Microparticles Co-Coated at 4% Solids[+] | | | | | | |
|---|---|---|---|---|---|---|---|
| | HC43H Ag | | | | | | |
| | 40 µg/ml | 80 µg/ml | 120 µg/ml | 40 µg/ml | 80 µg/ml | 120 µg/ml | |
| | | | 9NB44H Ag | | | | Commercially |
| | 40 µg/ml | 40 µg/ml | 40 µg/ml | 20 µg/ml | 20 µg/ml | 20 µg/ml | Available Microparticles |
| Panel B (anti-NS3) | 73,924 (2.59) | 91,008 (3.02) | 87,284 (3.02) | 68,454 (2.45) | 86,147 (2.96) | 94,439 (3.05) | 75,544 (2.93) |
| Anti-NS4 | 36,067 (1.26) | 47,685 (1.58) | 39,430 (1.36) | 23,967 (0.86) | 11,420 (0.39) | 16,177 (0.52) | 45,522 (1.76) |

[+] = a microparticle suspension contain

```
tct gaa cgt tct cag ccg cgt ggg cgt cgt cag ccg atc ccg aaa gct      193
Ser Glu Arg Ser Gln Pro Arg Gly Arg Arg Gln Pro Ile Pro Lys Ala
            50                  55                  60 cgt cgt ccg gaa ggt cgt acc tgg gct cag ccg ggt tac ccg tgg ccg      241
Arg Arg Pro Glu Gly Arg Thr Trp Ala Gln Pro Gly Tyr Pro Trp Pro
        65                  70                  75 ctg tac ggt aac gaa ggt tgc ggt tgg gct ggt tgg ctg ctg tct ccg      289
Leu Tyr Gly Asn Glu Gly Cys Gly Trp Ala Gly Trp Leu Leu Ser Pro
    80                  85                  90 cgt gga tct cgt ccg tct tgg ggt ccg acc gac ccg cgt cgt cgt tct      337
Arg Gly Ser Arg Pro Ser Trp Gly Pro Thr Asp Pro Arg Arg Arg Ser
95                  100                 105                 110 cgt aac ctt ggt aaa gtt atc gat acc ctg tct ggt aaa ccg gcc att      385
Arg Asn Leu Gly Lys Val Ile Asp Thr Leu Ser Gly Lys Pro Ala Ile
                115                 120                 125 atc ccg gac cgt gaa gtt ctg tac cgt gag ttc gac gaa atg gaa gaa      433
Ile Pro Asp Arg Glu Val Leu Tyr Arg Glu Phe Asp Glu Met Glu Glu
            130                 135                 140 tgc tct cag cac ctg ccg tac atc gaa cag ggt atg atg ctg gct gaa      481
Cys Ser Gln His Leu Pro Tyr Ile Glu Gln Gly Met Met Leu Ala Glu
        145                 150                 155 cag ttc aaa cag aaa gct ctg ggt ctg ctg cag acc gct tct tgg atg      529
Gln Phe Lys Gln Lys Ala Leu Gly Leu Leu Gln Thr Ala Ser Trp Met
    160                 165                 170 aac cgt ctg atc gct ttc gct tct cgt ggt aac cac gtt tct cca acc      577
Asn Arg Leu Ile Ala Phe Ala Ser Arg Gly Asn His Val Ser Pro Thr
175                 180                 185                 190 cac tac gtt ccg gaa tcg gac gct cat cat cac cat cac cat tgaggatcc   628
His Tyr Val Pro Glu Ser Asp Ala His His His His His His
                195                 200

<210> SEQ ID NO 2
<211> LENGTH: 204
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Gln Lys Lys Asn Lys Arg Asn Thr Asn Arg Arg Pro Gln Asp Val
1               5                   10                  15

Lys Phe Pro Gly Gly Gly Gln Ile Val Gly Gly Val Tyr Leu Leu Pro
            20                  25                  30

Arg Arg Gly Pro Arg Leu Gly Val Arg Ala Thr Arg Lys Thr Ser Glu
        35                  40                  45

Arg Ser Gln Pro Arg Gly Arg Arg Gln Pro Ile Pro Lys Ala Arg Arg
    50                  55                  60

Pro Glu Gly Arg Thr Trp Ala Gln Pro Gly Tyr Pro Trp Pro Leu Tyr
65                  70                  75                  80

Gly Asn Glu Gly Cys Gly Trp Ala Gly Trp Leu Leu Ser Pro Arg Gly
                85                  90                  95

Ser Arg Pro Ser Trp Gly Pro Thr Asp Pro Arg Arg Arg Ser Arg Asn
            100                 105                 110

Leu Gly Lys Val Ile Asp Thr Leu Ser Gly Lys Pro Ala Ile Ile Pro
        115                 120                 125

Asp Arg Glu Val Leu Tyr Arg Glu Phe Asp Glu Met Glu Glu Cys Ser
    130                 135                 140

Gln His Leu Pro Tyr Ile Glu Gln Gly Met Met Leu Ala Glu Gln Phe
```

```
                       145                 150                 155                 160
Lys Gln Lys Ala Leu Gly Leu Leu Gln Thr Ala Ser Trp Met Asn Arg
                165                 170                 175

Leu Ile Ala Phe Ala Ser Arg Gly Asn His Val Ser Pro Thr His Tyr
            180                 185                 190

Val Pro Glu Ser Asp Ala His His His His His His
        195                 200

<210> SEQ ID NO 3
<211> LENGTH: 1303
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (8)..(1294)

<400> SEQUENCE: 3 gaattcc atg gct gtt gac ttt atc ccg gtt gaa aat ctc gag act act         49
        Met Ala Val Asp Phe Ile Pro Val Glu Asn Leu Glu Thr Thr
        1               5                   10 atg cgt tct ccg gtt ttc act gac aac tct tct ccg ccg gtt gtt ccg         97
Met Arg Ser Pro Val Phe Thr Asp Asn Ser Ser Pro Pro Val Val Pro
15                  20                  25                  30 cag tct ttc cag gtt gct cac ctg cat gct ccg act ggt tct ggt aaa        145
Gln Ser Phe Gln Val Ala His Leu His Ala Pro Thr Gly Ser Gly Lys
                35                  40                  45 tct act aaa gtt cca gct gct tac gct gct cag ggt tac aaa gtt ctg        193
Ser Thr Lys Val Pro Ala Ala Tyr Ala Ala Gln Gly Tyr Lys Val Leu
            50                  55                  60 gtt ctg aac ccg tct gtt gct gct act ctg ggt ttc ggc gcc tac atg        241
Val Leu Asn Pro Ser Val Ala Ala Thr Leu Gly Phe Gly Ala Tyr Met
        65                  70                  75 tct aaa gct cac ggt atc gac ccg aac att cgt act ggt gta cgt act        289
Ser Lys Ala His Gly Ile Asp Pro Asn Ile Arg Thr Gly Val Arg Thr
80                  85                  90 atc act act ggt tct ccg atc act tac tct act tac ggt aaa ttc ctg        337
Ile Thr Thr Gly Ser Pro Ile Thr Tyr Ser Thr Tyr Gly Lys Phe Leu
95                  100                 105                 110 gct gac ggt ggt tgc tct ggt ggt gct tac gat atc atc atc tgc gac        385
Ala Asp Gly Gly Cys Ser Gly Gly Ala Tyr Asp Ile Ile Ile Cys Asp
                115                 120                 125 gaa tgc cac tct act gac gct act tct atc ctg ggt atc ggt acc gtt        433
Glu Cys His Ser Thr Asp Ala Thr Ser Ile Leu Gly Ile Gly Thr Val
            130                 135                 140 ctg gac cag gct gaa act gca ggt gct cgt ctg gtt gtt ctg gct act        481
Leu Asp Gln Ala Glu Thr Ala Gly Ala Arg Leu Val Val Leu Ala Thr
        145                 150                 155 gct act ccg ccg ggt tct gtt act gtt ccg cac ccg aac atc gaa gaa        529
Ala Thr Pro Pro Gly Ser Val Thr Val Pro His Pro Asn Ile Glu Glu
    160                 165                 170 gtt gct ctg tcg act act ggt gaa atc ccg ttc tac ggt aaa gct atc        577
Val Ala Leu Ser Thr Thr Gly Glu Ile Pro Phe Tyr Gly Lys Ala Ile
175                 180                 185                 190 ccg ctc gag gtt atc aaa ggt ggt cgt cac ctg att ttc tgc cac tct        625
Pro Leu Glu Val Ile Lys Gly Gly Arg His Leu Ile Phe Cys His Ser
                195                 200                 205 aaa aaa aaa tgc gac gaa ctg gct gct aag ctt gtt gct ctg ggt atc        673
Lys Lys Lys Cys Asp Glu Leu Ala Ala Lys Leu Val Ala Leu Gly Ile
```

```
aac gct gtt gct tac tac cgt ggt ctg gac gtt tct gtt atc ccg act    721
Asn Ala Val Ala Tyr Tyr Arg Gly Leu Asp Val Ser Val Ile Pro Thr
            225                 230                 235 tct ggt gac gtt gtt gtt gtg gcc act gac gct ctg atg act ggt tac    769
Ser Gly Asp Val Val Val Val Ala Thr Asp Ala Leu Met Thr Gly Tyr
    240                 245                 250 act ggt gac ttc gac tct gtt atc gat tgc aac act tgc aat tcc atg    817
Thr Gly Asp Phe Asp Ser Val Ile Asp Cys Asn Thr Cys Asn Ser Met
255                 260                 265                 270 tct acc aac ccg aaa ccg cag aaa aaa aac aaa cgt aac acc aac cgt    865
Ser Thr Asn Pro Lys Pro Gln Lys Lys Asn Lys Arg Asn Thr Asn Arg
                275                 280                 285 cgt ccg cag gac gtt aaa ttc ccg ggt ggt ggt cag atc gtt ggt ggt    913
Arg Pro Gln Asp Val Lys Phe Pro Gly Gly Gly Gln Ile Val Gly Gly
            290                 295                 300 gtt tac ctg ctg ccg cgt cgt ggt ccg cgt ctg ggt gtt cgt gct acg    961
Val Tyr Leu Leu Pro Arg Arg Gly Pro Arg Leu Gly Val Arg Ala Thr
        305                 310                 315 cgt aaa acc tct gaa cgt tct cag ccg cgt ggg cgt cgt cag ccg atc   1009
Arg Lys Thr Ser Glu Arg Ser Gln Pro Arg Gly Arg Arg Gln Pro Ile
320                 325                 330 ccg aaa gct cgt cgt ccg gaa ggt cgt acc tgg gct cag ccg ggt tac   1057
Pro Lys Ala Arg Arg Pro Glu Gly Arg Thr Trp Ala Gln Pro Gly Tyr
335                 340                 345                 350 ccg tgg ccg ctg tac ggt aac gaa ggt tgc ggt tgg gct ggt tgg ctg   1105
Pro Trp Pro Leu Tyr Gly Asn Glu Gly Cys Gly Trp Ala Gly Trp Leu
                355                 360                 365 ctg tct ccg cgt gga tct cgt ccg tct tgg ggt ccg acc gac ccg cgt   1153
Leu Ser Pro Arg Gly Ser Arg Pro Ser Trp Gly Pro Thr Asp Pro Arg
            370                 375                 380 cgt cgt tct cgt aac ctt ggt aaa gtt atc gat acc ctg acc tgc ggt   1201
Arg Arg Ser Arg Asn Leu Gly Lys Val Ile Asp Thr Leu Thr Cys Gly
        385                 390                 395 ttc gct gac ctg atg ggt tac ata ccg ctg gtt gga gct ccg ctg ggt   1249
Phe Ala Asp Leu Met Gly Tyr Ile Pro Leu Val Gly Ala Pro Leu Gly
400                 405                 410 ggt gct gct cgt gct ggt tct ggc agc cat cat cac cat cac cat        1294
Gly Ala Ala Arg Ala Gly Ser Gly Ser His His His His His His
415                 420                 425 tgaggatcc                                                          1303
```

<210> SEQ ID NO 4
<211> LENGTH: 429
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Ala Val Asp Phe Ile Pro Val Glu Asn Leu Glu Thr Thr Met Arg
1               5                   10                  15

Ser Pro Val Phe Thr Asp Asn Ser Ser Pro Val Val Pro Gln Ser
            20                  25                  30

Phe Gln Val Ala His Leu His Ala Pro Thr Gly Ser Gly Lys Ser Thr
        35                  40                  45

Lys Val Pro Ala Ala Tyr Ala Ala Gln Gly Tyr Lys Val Leu Val Leu
    50                  55                  60

Asn Pro Ser Val Ala Ala Thr Leu Gly Phe Gly Ala Tyr Met Ser Lys
65                  70                  75                  80

Ala His Gly Ile Asp Pro Asn Ile Arg Thr Gly Val Arg Thr Ile Thr
            85                  90                  95

Thr Gly Ser Pro Ile Thr Tyr Ser Thr Tyr Gly Lys Phe Leu Ala Asp
        100                 105                 110

Gly Gly Cys Ser Gly Gly Ala Tyr Asp Ile Ile Cys Asp Glu Cys
        115                 120                 125

His Ser Thr Asp Ala Thr Ser Ile Leu Gly Ile Gly Thr Val Leu Asp
    130                 135                 140

Gln Ala Glu Thr Ala Gly Ala Arg Leu Val Val Leu Ala Thr Ala Thr
145                 150                 155                 160

Pro Pro Gly Ser Val Thr Val Pro His Pro Asn Ile Glu Glu Val Ala
                165                 170                 175

Leu Ser Thr Thr Gly Glu Ile Pro Phe Tyr Gly Lys Ala Ile Pro Leu
            180                 185                 190

Glu Val Ile Lys Gly Gly Arg His Leu Ile Phe Cys His Ser Lys Lys
        195                 200                 205

Lys Cys Asp Glu Leu Ala Ala Lys Leu Val Ala Leu Gly Ile Asn Ala
210                 215                 220

Val Ala Tyr Tyr Arg Gly Leu Asp Val Ser Val Ile Pro Thr Ser Gly
225                 230                 235                 240

Asp Val Val Val Ala Thr Asp Ala Leu Met Thr Gly Tyr Thr Gly
                245                 250                 255

Asp Phe Asp Ser Val Ile Asp Cys Asn Thr Cys Asn Ser Met Ser Thr
            260                 265                 270

Asn Pro Lys Pro Gln Lys Lys Asn Lys Arg Asn Thr Asn Arg Arg Pro
        275                 280                 285

Gln Asp Val Lys Phe Pro Gly Gly Gln Ile Val Gly Gly Val Tyr
        290                 295                 300

Leu Leu Pro Arg Arg Gly Pro Arg Leu Gly Val Arg Ala Thr Arg Lys
305                 310                 315                 320

Thr Ser Glu Arg Ser Gln Pro Arg Gly Arg Arg Gln Pro Ile Pro Lys
                325                 330                 335

Ala Arg Arg Pro Glu Gly Arg Thr Trp Ala Gln Pro Gly Tyr Pro Trp
            340                 345                 350

Pro Leu Tyr Gly Asn Glu Gly Cys Gly Trp Ala Gly Trp Leu Leu Ser
        355                 360                 365

Pro Arg Gly Ser Arg Pro Ser Trp Gly Pro Thr Asp Pro Arg Arg Arg
    370                 375                 380

Ser Arg Asn Leu Gly Lys Val Ile Asp Thr Leu Thr Cys Gly Phe Ala
385                 390                 395                 400

Asp Leu Met Gly Tyr Ile Pro Leu Val Gly Ala Pro Leu Gly Gly Ala
                405                 410                 415

Ala Arg Ala Gly Ser Gly Ser His His His His His
            420                 425

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 5

```
His His His His His His
1               5

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ser Gly Ser
1
```

What is claimed is:

1. An immunodiagnostic reagent consisting essentially of
   (a) an isolated or purified polypeptide consisting essentially of the contiguous amino acids 1-198 of SEQ ID NO:2 or a contiguous amino acid sequence that is at least 95% identical to the contiguous amino acids 1-198 of SEQ ID NO: 2 and
   (b) an isolated or purified polypeptide consisting essentially of (i) an epitope that is immunoreactive with an antibody that specifically binds to the NS3 region of HCV and (ii) an epitope that is immunoreactive with an antibody that specifically binds to the core region of HCV, wherein the isolated or purified polypeptide consists essentially of the contiguous amino acids 2-267 and 270-419 of SEQ ID NO:4,
   wherein (a) and (b) are co-coated on the same microparticles in a ratio of about 1:2 and concentration of (a) is at least about 40 μg/mL and the concentration of (b) is at least about 80 μg/mL.

2. A kit consisting of the immunodiagnostic reagent of claim 1 and instructions for the use of the immunodiagnostic reagent in the immunoassay of anti-HCV antibodies.

3. A method of determining the presence, amount, or concentration of anti-HCV antibodies in a test sample, which method comprises assaying the test sample for anti-HCV antibodies by an assay:
   (i) employing:
   (i') an immunodiagnostic reagent comprising at least one pair of first specific binding partners selected from the group consisting of
   (1) an isolated or purified polypeptide consisting essentially of the contiguous amino acids 1-198 of SEQ ID NO: 2 or a contiguous amino acid sequence that is at least 95% identical to the contiguous amino acids 1-198 of SEQ ID NO: 2 and an isolated or purified polypeptide comprising an epitope that is immunoreactive with an antibody that specifically binds to the NS3 region of HCV,
   (2) an isolated or purified polypeptide consisting essentially of the contiguous amino acids 1-198 of SEQ ID NO: 2 or a contiguous amino acid sequence that is at least 95% identical to the contiguous amino acids 1-198 of SEQ ID NO: 2 and an isolated or purified polypeptide comprising the contiguous amino acids 2-267 of SEQ ID NO:4,
   (3) an isolated or purified polypeptide consisting essentially of the contiguous amino acids 1-198 of SEQ ID NO: 2 or a contiguous amino acid sequence that is at least 95% identical to the contiguous amino acids 1-198 of SEQ ID NO: 2 and an isolated or purified polypeptide comprising an epitope that is immunoreactive with an antibody that specifically binds to the NS3 region of HCV and an epitope that is immunoreactive with an antibody that specifically binds to the core region of HCV, and
   (4) an isolated or purified polypeptide consisting essentially of the contiguous amino acids 1-198 of SEQ ID NO: 2 or a contiguous amino acid sequence that is at least 95% identical to the contiguous amino acids 1-198 of SEQ ID NO: 2 and an isolated or purified polypeptide comprising the contiguous amino acids 2-267 and 270-419 of SEQ ID NO:4, and
   (ii') at least one detectable label, and
   (ii) comprising:
   comparing a signal generated by the detectable label as a direct or indirect indication of the presence, amount or concentration of anti-HCV antibodies in the test sample to a signal generated as a direct or indirect indication of the presence, amount or concentration of anti-HCV antibodies in a control or calibrator, which is optionally part of a series of calibrators in which each of the calibrators differs from the other calibrators in the series by the concentration of anti-HCV antibodies, whereupon the presence, amount or concentration of anti-HCV antibodies in the test sample is determined,
   wherein the polypeptides of which the immunodiagnostic reagent is comprised are co-coated on the same microparticles in a ratio of about 1:2 and the concentration of the isolated or purified polypeptide consisting essentially of the contiguous amino acids 1-198 of SEQ ID NO: 2 or a contiguous amino acid sequence that is at least about 95% identical to the contiguous amino acids 1-198 of SEQ ID NO: 2 is at least about 40 μg/mL and the concentration of the other isolated or purified polypeptide is at least about 80 μg/mL.

4. The method of claim 3, which comprises the following steps:
   (i) contacting the test sample with the immunodiagnostic reagent so as to form first specific binding partner/anti-HCV antibody complexes,
   (ii) contacting the first specific binding partner/anti-HCV antibody complexes with at least one detectably labeled second specific binding partner for anti-HCV antibody so as to form first specific binding partner/anti-HCV antibody/second specific binding partner complexes, and
   (iii) determining the presence, amount or concentration of anti-HCV antibodies in the test sample by detecting or measuring the signal generated by the detectable label in the first specific binding partner/anti-HCV antibody/second specific binding partner complexes formed in (ii), whereupon the presence, amount or concentration of anti-HCV antibodies in the test sample is determined.

5. The method of claim 3, which comprises the following steps:
(i) contacting the test sample with the immunodiagnostic reagent and simultaneously or sequentially, in either order, contacting the test sample with at least one detectably labeled second specific binding partner, which can compete with anti-HCV antibody for binding to the at least one pair of first specific binding partners and which comprises detectably labeled anti-HCV antibodies, wherein any anti-HCV antibody present in the test sample and the at least one detectably labeled second specific binding partner compete with each other to form first specific binding partner/anti-HCV antibody complexes and a first specific binding partner/second specific binding partner complexes, respectively, and
(ii) determining the presence, amount or concentration of anti-HCV antibodies in the test sample by detecting or measuring the signal generated by the detectable label in the first specific binding partner/second specific binding partner complex formed in (ii), wherein the signal generated by the detectable label in the first specific binding partner/second specific binding partner complex is inversely proportional to the amount or concentration of anti-HCV antibodies in the test sample, whereupon the presence, amount or concentration of anti-HCV antibodies in the test sample is determined.

6. The method of claim 3, wherein the test sample was obtained from a patient and the method further comprises diagnosing, prognosticating, or assessing the efficacy of a therapeutic/prophylactic treatment of the patient, wherein, if the method further comprises assessing the efficacy of a therapeutic/prophylactic treatment of the patient, the method optionally further comprises modifying the therapeutic/prophylactic treatment of the patient as needed to improve efficacy.

7. The method of claim 3, wherein the method is adapted for use in an automated system or a semi-automated system.

* * * * *